(12) United States Patent
Vandali et al.

(10) Patent No.: US 9,084,893 B2
(45) Date of Patent: Jul. 21, 2015

(54) ENHANCED ENVELOPE ENCODED TONE, SOUND PROCESSOR AND SYSTEM

(75) Inventors: Andrew Vandali, Greenvale (AU); Richard Van Hoesel, Reservoir (AU)

(73) Assignee: HEARWORKS PTY LTD, Melbourne, Victoria (AU)

( * ) Notice: Subject to any disclaimer, the term of this patent is extended or adjusted under 35 U.S.C. 154(b) by 889 days.

(21) Appl. No.: 13/147,585

(22) PCT Filed: Feb. 3, 2010

(86) PCT No.: PCT/AU2010/000104
§ 371 (c)(1),
(2), (4) Date: Aug. 2, 2011

(87) PCT Pub. No.: WO2010/088722
PCT Pub. Date: Aug. 12, 2010

(65) Prior Publication Data
US 2011/0286618 A1    Nov. 24, 2011

(30) Foreign Application Priority Data
Feb. 3, 2009    (AU) ................................ 2009900365

(51) Int. Cl.
*H04R 25/00*    (2006.01)
*A61N 1/36*    (2006.01)
(Continued)

(52) U.S. Cl.
CPC ............ *A61N 1/36032* (2013.01); *G10L 25/90* (2013.01); *G10L 2021/065* (2013.01)

(58) Field of Classification Search
CPC .. H04R 25/502; H04R 25/356; H04R 25/505; H04R 25/453; H04R 25/606; A61N 1/36032; A61N 1/0541; A61N 1/08; A61F 11/04
USPC ............................................ 381/320; 607/57
See application file for complete search history.

(56) References Cited

U.S. PATENT DOCUMENTS

| 5,597,380 A | 1/1997 | McDermott et al. |
| 7,076,308 B1 | 7/2006 | Overstreet et al. |

(Continued)

FOREIGN PATENT DOCUMENTS

| AU | 657959 | 1/1993 |
| WO | 2008011680 A1 | 1/2008 |

OTHER PUBLICATIONS

International Search Report dated Mar. 1, 2010 for corresponding International Application No. PCT/AU2010/000104, filed Feb. 3, 2010.

(Continued)

*Primary Examiner* — Simon Sing
(74) *Attorney, Agent, or Firm* — Westman, Champlin & Koehler, P.A.

(57) ABSTRACT

There is disclosed a system (20) for processing sound signals for use in a hearing prosthesis, the system comprising a transducer (1) for converting a sound signal into an electrical signal (30). A first. processor (4) for processing said electrical signal (30) into a plurality of frequency channel signals, each channel signal having an amplitude envelope to define at least one set of channel outputs (40, 41). A second processor (5) for obtaining information relating to a fundamental frequency of the electrical Signal (30). A third processor (6) for obtaining information relating to the harmonic nature of the electrical signal (30). A modulator (7) for modulating the at least one set of channel outputs (40, 41) received from the first processor (4) in accordance with the in formation relating to the fundamental frequency and the harmonic nature of, the electrical signal so as to generate at least one modified set of channel outputs (70, 71). A selector (8) for selecting one or more channels from the at least one modified set of channel outputs (70, 71) so as to define at least one or more channels for electrical stimulation together with the magnitude of said electrical stimulation and generating a stimulation signal (80, 81) in accordance therewith, A transmitter (10) for transmitting said stimulation signal for application by said hearing prosthesis (11).

21 Claims, 14 Drawing Sheets

(51) Int. Cl.
*G10L 25/90* (2013.01)
*G10L 21/06* (2013.01)

(56) References Cited

U.S. PATENT DOCUMENTS

| | | | |
|---|---|---|---|
| 7,130,694 | B1 | 10/2006 | Voelkel |
| 7,561,709 | B2 | 7/2009 | Vandali et al. |
| 8,027,733 | B1 * | 9/2011 | Fridman et al. ............ 607/57 |
| 2005/0107843 | A1 | 5/2005 | McDermott et al. |
| 2005/0197832 | A1 | 9/2005 | Vandali et al. |
| 2006/0013422 | A1 | 1/2006 | Goorevich et al. |
| 2006/0080087 | A1 * | 4/2006 | Vandali et al. ............ 704/207 |
| 2007/0118359 | A1 | 5/2007 | Vandali et al. |

OTHER PUBLICATIONS

Written Opinion of the International Searching Authority dated Mar. 5, 2010 for corresponding International Application No. PCT/AU2010/000104, filed Feb. 3, 2010.

\* cited by examiner

ENHANCED ENVELOPE ENCODED TONE, SOUND PROCESSOR AND SYSTEM

CROSS REFERENCE TO RELATED APPLICATIONS

This application is the National Stage of International Application Number PCT/AU2010/000104 filed on Feb. 3, 2010, which claims priority under 35 USC §119 (a)-(d) of Patent Application No. 2009900365 filed in Australia on Feb. 3, 2009, the contents of which are incorporated herein by reference.

FIELD OF INVENTION

This invention relates to a system and method of processing signals derived from sound signals, and in particular, to a system and method of processing signals derived from sound signals for the generation of stimuli in auditory prostheses, such as cochlear implants and other systems requiring vocoder based sound processing or encoding.

BACKGROUND OF THE INVENTION

Cochlear implants have proven to be clinically effective in providing the sensation of hearing to individuals with a profound hearing loss. Such devices typically comprise an array of implantable electrodes located within the cochlea of the individual which directly apply electrical stimulation to the surviving auditory neural elements which are perceived by the brain as sounds. The electrical stimulation applied to the auditory pathway of the individual is derived from an acoustic signal which is processed by a sound processor according to a variety of sound processing strategies.

Traditionally, most early sound processing strategies have concentrated on processing the acoustic signal in a manner that enables the recipient to obtain some degree of open-set speech discrimination. As such, existing sound processing strategies have been successful in enabling the recipient to understand conversation speech in quiet surroundings without the aid of lip reading. However, studies comparing normal hearing to cochlear implant listening have shown that voice pitch is poorly perceived by users of cochlear implants. In addition, pitch information which forms the basis for melody in music has also been shown to be poorly perceived by users of cochlear implants.

Voice pitch information can play an important role in speech perception. Voice pitch information can provide important cues to linguistic features of speech, such as intonation to assist a listener in determining the contrast between a question or a statement being made by a speaker, as well as any emphasis that may be placed on a word or words by the speaker. Voice pitch information can also provide important cues to paralinguistic features of speech, to aid in speaker identification and the determination of the emotional state of the speaker, as well as assisting the listener to segregate concurrent speakers.

Most importantly, it bis been established that voice pitch information is crucial for perception of tonal languages, such as Mandarin and Cantonese, where a change in fundamental voicing frequency within the same phonemic segment causes a change in lexical moaning.

Various sound processing strategies have been developed for processing of sound signals for use in stimulating auditory prostheses, such as cochlear implants. One such strategy, referred to as a "multi-peak strategy", focuses particularly on coding of aspects of speech, such as formants and the fundamental voicing frequency (F0). For this strategy, voice pitch information has been predominantly coded by way of the electrical stimulation rate. However, whilst results with this strategy have shown that pitch could be perceived, performance deteriorates rapidly in real world situations, especially in the presence of noise. Other strategies have been proposed that code voice-pitch information (for voicing frequencies up to approximately 300 Hz) by way of amplitude modulation, at a frequency equal to or related, to the voicing frequency, in the envelope of the electrical stimulus signals. These strategies include the Spectral Maxima Sound Processor (SMSP) strategy (which is described in greater detail in Australian Patent No. 657959 and U.S. Pat. No. 5,597,380 by McDermott & Vandali, 1991), and more recent implementations of this strategy known as the Spectral Peak (SPEAK) strategy (Skinner et al., 1994; Whitford et al., 1995), and the Advanced Combinational Encoder (ACE) strategy (Vandali et al., 2000; Skinner et al., 2002). However, studies examining pitch perception with these strategies have shown that the salience and accuracy or cues to pitch can be poor for some signals and in real world situations and performance deteriorates rapidly in noise.

A number of modifications to existing sound coding strategies have been proposed in an attempt to improve coding of voice and/or musical pitch. These include the Modulation Depth Enhancement (MDE) and Multi-channel Envelope Modulation (MEM) strategies described in Vandali et al., 2005 and disclosed in US Patent Publication No. 20060080087; Vandali, A. E., and van Hoesel, R. J. "Modulation depth enhancement for tone perception," U.S. Pat. No. 7,561,709; and Vandali, A. E., van Hoesel, R. J., and Seligman, P. M. "Pitch perception in an auditory prosthesis," US continuation-in-part patent application of US patent application US 2006/0080087. In addition, McDermott and McKay proposed a device for improving coding of pitch in cochlear implant systems (McDermott, H., and McKay, C. "Cochlear Implant Sound Processing Method and System", US patent application US 2005/0107843. Each of these documents is incorporated herein by reference.

Despite the above attempts to improve the coding of voice and/or musical pitch particularly for use in stimulating auditory prosthesis, there is still a need to improve such perception in a range of hearing situations. As such, the present invention addresses this need by creating a complete system that codes voice and/or musical pitch information in a cochlear implant system in an effective manner which is robust to the effects of competing noise and/or interfering signals.

The above references to and descriptions of prior proposals or products are not intended to be, and are not to be construed as, statements or admissions of common general knowledge in the art. In particular, the following prior art discussion does not relate to what is commonly or well known by the person skilled in the art, but assists in the understanding of the inventive step of the present invention of which the identification of pertinent prior art proposals is but one part.

STATEMENT OF INVENTION

In a first aspect, the present invention provides a method for processing sound signals for use in a hearing prosthesis, comprising:
converting said sound signal into an electrical signal;
processing said electrical signal into a plurality of frequency channel signals, each channel signal having an amplitude envelope to define at least one set of channel outputs;
obtaining information relating to the fundamental frequency of the electrical signal;

obtaining information relating to the harmonic nature of the electrical signal;

modulating the at least one set of channel outputs in accordance with the information relating to the fundamental frequency and the harmonic nature of the electrical signal so as to generate art least one modified set of channel outputs;

selecting one or more channels from the at least one modified set of channel outputs to define at least one or more channels for electrical stimulation by a corresponding electrode of the hearing prosthesis, as well as the magnitude of said electrical stimulation.

In one embodiment, the step of converting said sound signal into an electrical signal includes employing a microphone to detect and convert the sound signal into an electrical signal. The electrical signal may be further amplified and then sampled by passing the electrical signal through an analog-to digital converter to generate a sampled signal.

In another embodiment, the step of processing the electrical signal into a plurality of frequency channel signals includes passing the electrical signal through a first bank of hand pass filters. Each frequency channel signal may then be passed through an envelope detector to produce a set of corresponding channel envelope signals as a set of first channel outputs.

Each channel envelope signal of the set of first channel outputs may be smoothed in time by a channel envelope tracker to derive slow moving channel envelope signals as a set of second channel outputs. The channel envelope tracker may operate as a form of a low-pass filter to smooth frequency components above approximately 70 Hz in each channel envelope signal.

The step of processing the electrical, signal into a plurality of frequency channel signals may further include passing the electrical signal through a second bank of band pass filters. The second bank of band pass filters may have substantially the same centre frequencies as the first bank of band pass filters and each filter may be sufficiently wide so as to pass at least two fundamental frequency harmonics of the highest fundamental frequency determined in relation to the electrical frequency to produce a plurality of wide-bandwidth channel signals. Each of the wide-bandwidth channel signals may be passed through an envelope detector to derive a plurality of resultant wide-bandwidth channel envelope signals as a set of third channel outputs.

In another embodiment, the step of obtaining information relating to the fundamental frequency of the electrical signal comprises passing the electrical signal through a Fundamental Frequency Estimator. The Fundamental frequency Estimator may be a phase-vocoder FFT filterbank that processes the electrical signal to provide an estimate of the frequency and power of any sinusoidal frequency components present in the electrical signal up to a frequency of around 2 kHz. The Fundamental Frequency Estimator may determine the fundamental frequency of the most dominant harmonic signal detected in the electrical signal and may generate a signal representative of the estimation of that most dominant fundamental frequency. The Fundamental Frequency Estimator may further generate a signal representative of the ratio of the power related to the most dominant fundamental frequency to the total signal power present in the electrical signal, up to a frequency of around 2 kHz.

In another embodiment, the step of obtaining information relating to the harmonic nature of the electrical signal comprises passing the signal representative of the ratio of the power related to the most dominant fundamental frequency to the total signal power present in the electrical signal, to a Periodic Probability Estimator. The Periodic Probability Estimator may derive a periodic probability value for the input signal (up to 2 kHz) by compression limiting and smoothing the signal representative or the ratio of the power related to the most dominant fundamental frequency to the total signal power present in the electrical signal.

In another embodiment, the step of obtaining information relating to the harmonic nature of the electrical signal comprises passing the frequency and power of any sinusoidal frequency components present in the electrical signal and the set of third channel outputs, to the Periodic Probability Estimator. The Periodic Probability Estimator may estimate the probability that the signal in any frequency channel is related to the estimated most dominant fundamental frequency of the electrical signal and may generate a channel periodic probability signal for each channel.

In yet another embodiment, the step of modulating the at least one set of channel outputs in accordance with the information relating to the fundamental frequency and the harmonic nature of the electrical signal so as to generate at least one modified set of channel outputs is performed by a channel modulator. The channel modulator may receive the set of second channel outputs and may modulate the signals by a periodic modulation function substantially equal to the estimated most dominant fundamental frequency of the electrical signal as provided by the Fundamental Frequency Estimator. The modulated set of second channel outputs may be sealed by the channel periodic probability signals determined by the Periodic Probability Estimator to produce a scaled and modulated set of second channel outputs.

The channel modulator may further receive the set of first channel outputs and may scale each first channel output by the channel non-periodic probability signals (i.e., one minus the channel periodic probability) determined for each channel to produce a scaled set of first channel outputs. The sealed set of first channel outputs may be further attenuated by the channel modulator, particularly when the input signal periodic probability value indicates that the input signal is periodic to produce a scaled and attenuated set of first channel outputs.

In one embodiment, the scaled and modulated set of second channel outputs may then be mixed with the scaled and attenuated set of first channel outputs to produce a modified set of fourth channel outputs. In another embodiment, the scaled and modulated sot of second channel outputs are mixed with the scaled set of first channel outputs to produce a set of restore channel envelope signals.

In yet another embodiment, the step of selecting one or more channels from the at least one modified set of channel outputs comprises selecting channels from the modified set of fourth channel outputs having a largest spectral magnitude. The selection of the channels having the largest spectral magnitude may be at least partially multiplexed across frames to increase the spectral range of channels selected and to introduce a greater spread in the selected maxima channels. The magnitude of selected channels having the largest spectral magnitudes may be restored from the magnitude of the set of restore channel envelope signals.

According to a second aspect, there is provided a method of processing sound signals for use in a hearing prosthesis, comprising:

converting said sound signal into an electrical signal;

processing said electrical signal into a plurality of frequency channel signals, each frequency channel signal having an amplitude envelope to define at least one set of channel outputs;

determining whether the electrical signal comprises harmonic and/or non-harmonic signals;

for portions of the electrical signal comprising harmonic signals, modulating a slow varying envelope of the channel outputs by a periodic function of frequency equal to the fundamental frequency of the harmonic signal to produce one or more modulated channel envelope signals;

for portions of the electrical signal comprising non-harmonic signals, producing one or more non-modulated channel envelope signals;

for each channel, mixing the modulated channel envelope signal and the non-modulated channel envelope signal in accordance with a predetermined mixing ratio to produce a mixed channel stimulation signal for each channel; and selecting one or more channels to define at least one or more channels for electrical stimulation and applying stimulation to a corresponding electrode of the hearing prosthesis, in accordance with the mixed channel stimulation signal.

In an embodiment, of this aspect of the invention, the predetermined mixing ratio is derived from a degree to which the frequency channel signal is related to the most dominant fundamental frequency in the electrical signal. Where there is a strong relationship between the frequency channel signal and the most dominant, fundamental frequency in the electrical signal, there may be a high mixing ratio. Further, where there is a weak relationship between the frequency channel signal and the most dominant fundamental frequency in the electrical signal, there may be a low mixing ratio.

According to a third aspect of the present invention, the present invention provides a system for processing sound signals for use in a hearing prosthesis, the system comprising: system for processing sound signals for use in a hearing prosthesis, the system comprising:

a transducer for converting a sound signal into an electrical signal;

a first processor for processing said electrical signal into a plurality of frequency channel signals, each channel signal having an amplitude envelope to define at least one set of channel outputs a second processor for obtaining information relating to a fundamental frequency of the electrical signal;

a third processor for obtaining information relating to the harmonic nature of the electrical signal;

a modulator for modulating the at least one set of channel outputs received from the first processor in accordance with the information relating to the fundamental frequency and the harmonic nature of the electrical signal so as to generate at least one modified set of channel outputs;

a selector for selecting one or more channels from the at least one modified sol of channel outputs so as to define at least one or more channels for electrical stimulation together with the magnitude of said electrical stimulation and generating a stimulation signal in accordance therewith; and a transmitter for transmitting said stimulation signal for application by said hearing prosthesis.

According to an embodiment of the third aspect of the present invention, the transducer comprises a microphone configured to detect and convert the sound signal into an electrical signal. The transducer may further comprise an amplifier to amplify the electrical signal and an analog-to digital converter to generate a sampled signal.

The first processor may comprise a first bank of band pass filters to process the electrical signal into a plurality of frequency channel signals. The first processor may further comprise an envelope detector. The envelope detector may be configured such that each channel signal is further passed through the envelope detector to produce a set of corresponding channel envelope signals as a set of first channel outputs. The first processor may further comprise a channel envelope tracker. The channel envelope tack or may be configured to receive each channel envelope signal of the set of first channel outputs to derive slow moving channel envelope signals as a set of second channel outputs.

The first processor may further comprise a second bank of band pass filters. The second hank of band pass filters may have substantially the same centre frequencies as the first bank of hand pass filters and may be sufficiently wide so as to pass at least two fundamental frequency harmonics of the highest fundamental frequency determined in relation to the electrical frequency to produce a plurality of wide-bandwidth channel signals. The first processor may also comprise a second envelope detector such that each of the wide-bandwidth channel signals may be passed through the second envelope detector to derive a plurality of resultant wide-bandwidth channel envelope signals as a set of third channel outputs.

The second processor may comprise a Fundamental Frequency Estimator. The Fundamental Frequency Estimator may be a phase-vocoder FFT filterbank that processes the electrical signal to provide an estimate of the frequency and power of any sinusoidal frequency components present in the electrical signal up to a frequency of around 2 kHz. The Fundamental Frequency Estimator may determine the fundamental frequency of the most dominant harmonic signal detected in the electrical signal up to a frequency of around 2 kHz and generates a signal representative of the estimation of the most dominant fundamental frequency. The Fundamental Frequency Estimator may further generate a signal representative of a ratio of the power related to the most dominant fundamental frequency to the total signal power present in the electrical signal up to a frequency of around 2 kHz.

The third processor may comprise a Periodic Probability Estimator that receives at least the signal representative of a ratio of the power related to the most dominant fundamental frequency to the total signal power present in the electrical signal. The Periodic Probability Estimator may derive an input signal periodic, probability value by compression limiting and smoothing the signal representative of the ratio of the power related to the most dominant fundamental frequency to the total signal power present in the electrical signal. A signal representative of the frequency and power of any sinusoidal frequency components present in the electrical signal, and the set of third channel outputs may be received by the Periodic Probability Estimator. The Periodic Probability Estimator may further estimate the probability that the signal in any frequency channel is related to the estimated most dominant fundamental frequency of the electrical signal and generates a channel periodic probability signal for each channel using the frequency and power of any sinusoidal frequency components present in the electrical signal determined from the Fundamental frequency Estimator, and the set of third channel outputs determined by the second bank of band pass filters.

The modulator may be a channel modulator that receives the set of second channel outputs and modulates said set of second channel outputs by a periodic modulation function substantially equal to the estimated most dominant fundamental frequency of the electrical signal as provided by the Fundamental Frequency Estimator. The modulated set of second channel outputs may be scaled by the channel periodic probability signals determined by the Periodic Probability Estimator for each channel to produce a scaled and modulated set of second channel outputs. The channel modulator may further receive the set of first channel outputs and scales each first channel output by one minus the channel periodic probability signals determined for each channel to produce a scaled set of first channel outputs. The scaled set of first channel outputs may be further attenuated by the channel modulator, particularly when the input signal periodic probability value indicates that the input signal is periodic, to produce a scaled and attenuated set of first channel outputs. The scaled and modulated set of second channel outputs may be mixed with the scaled and attenuated set of first channel outputs to produce a modified set of fourth channel outputs for each channel. The scaled and modulated set of second channel outputs may be mixed with the scaled set of first channel outputs to produce a set of restore channel envelope signals.

The selector may be a maxima selector that selects one or more channels from the at least one modified set of channel outputs based upon the outputs having a largest spectral magnitude. The maxima selector may further comprise a multiplexor such that the selection of the channels having the largest spectral magnitude is at least partially multiplexed across frames to increase the number of channels selected.

The transmitter may comprise an encoder that encodes the stimulation signal for transmission to an implanted stimulator. The transmitter may further comprise an RF transmitter that is configured to transmit the encoded stimulation signal in the form of an RF signal.

BRIEF DESCRIPTION OF THE DRAWINGS

Preferred features of the present invention will now be described with particular reference to the accompanying drawings. However, it is to be understood that the features illustrated in and described with reference to the drawings are not to be construed as limiting on the scope of the invention. In the drawings.

DETAILED DESCRIPTION OF THE DRAWINGS

The present invention will be described below in relation to its application for use with an implantable hearing prosthesis, such as a cochlear implant. However, it will be appreciated that the present invention may also have application to other vocoder based sound processing systems, and still fall within the spirit of the present invention.

Figure 1:
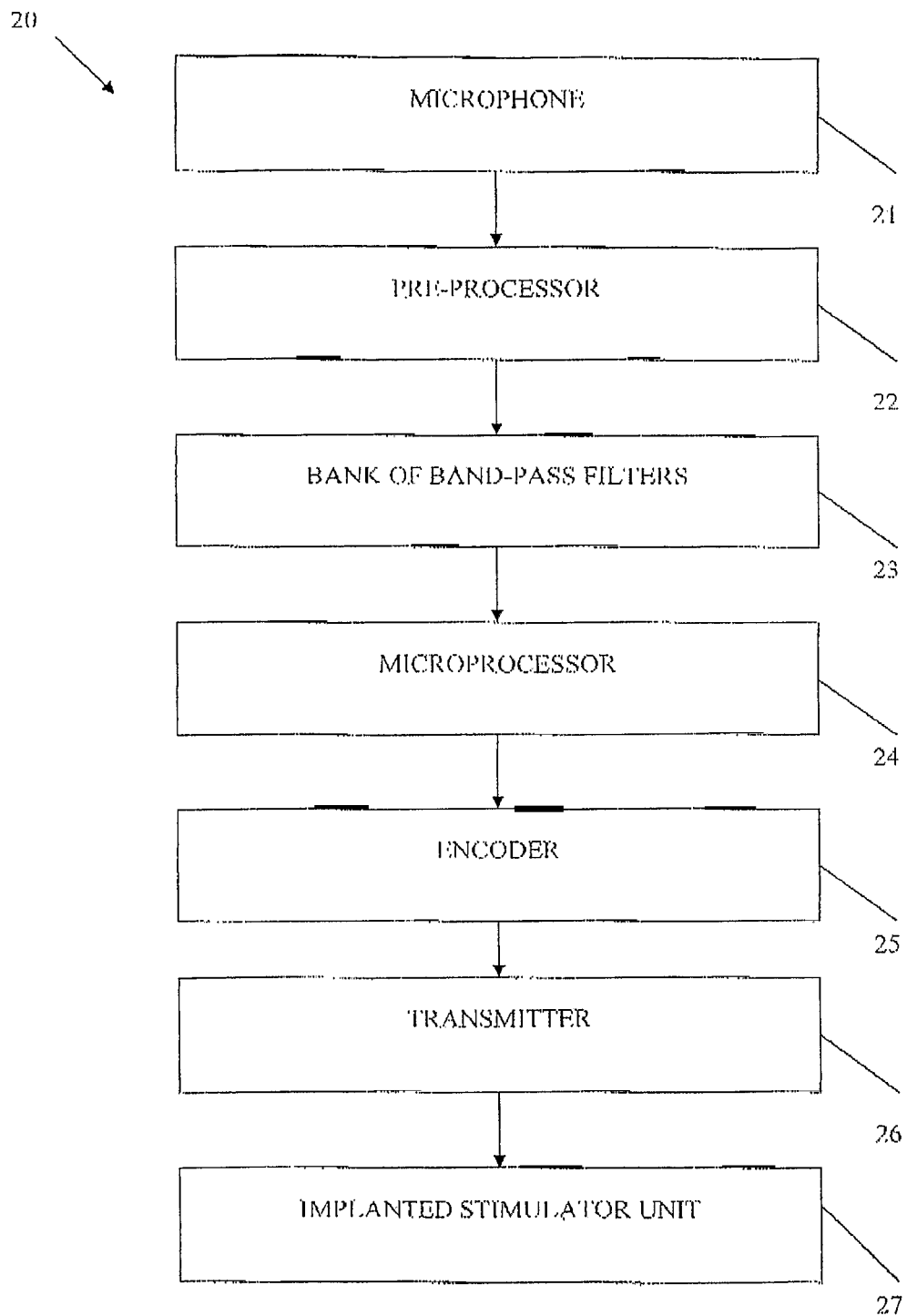
FIG. 1 is a simple block diagram showing a conventional sound processing system.

Referring to FIG. 1, a simplified block diagram of a conventional sound processing system 20 used with a conventional cochlear implant system is shown. A conventional cochlear implant system typically comprises an external speech processor that employs the sound processing system 20 to detect sound and convert the sound into signals which are transmitted to an implanted stimulator unit. The implanted stimulator unit then converts the received signals into electrical stimulation pulses which can be directly applied to the auditory pathway of the implant recipient to replicate the detected sound.

A variety of sound processing systems 20 have been proposed and employed with cochlear implant systems to various degrees of success. Examples of the different types of systems or strategies employed include the Advanced Combination Encoders (ACE) strategy, the Continuous Interleaved Sampling (CIS) strategy, and the Spectral Peak (SPEAK) strategy.

Generally, each system or strategy 20 employs a microphone 21 to detect and receive sound and generate a corresponding electrical signal. The electrical signal is then typically passed through a pre-processor 22 where the signal undergoes some pre-amplification and where required, is converted to a digital signal after passing through an analog-to-digital converter.

The pre-processed signal is then typically divided into a number of frequency channels by way of a bank 23 of band-pass filters. The number of channels may vary depending upon the specific strategy 20 employed, and the envelope of the signal in each channel is typically estimated. A microprocessor or digital signal processor 24 typically selects the largest channel amplitudes (or in the case of the CTS stimulation strategy, all of the channels) and the selected amplitudes are then typically converted into stimulus current levels. The stimulus current levels are typically mapped between audible threshold and maximum comfort levels for each electrode that corresponds to the selected frequency channel. In this regard the electrodes of the implanted stimulator are allocated to the frequency channels in a manner consistent with the tonotopical nature of the cochlea. The stimulus current levels are typically sent to an encoder 25 where spectral cues in the detected sound signal are typically encoded via electrode place and temporal envelope cues are encoded via amplitude fluctuations in the envelope of the stimulus signal. The encoded signal is then sent to a transmitter 26 where it is sent to the implanted stimulator unit 27, typically in the form of an RF signal.

Whilst the system 20 described above has been effective in achieving high levels of speech perception for recipients, the system 20 typically delivers limited spectral and temporal information derived from the sound which is typically not sufficient for satisfactory music and tone perception in cochlear implant recipients.

Figure 2:
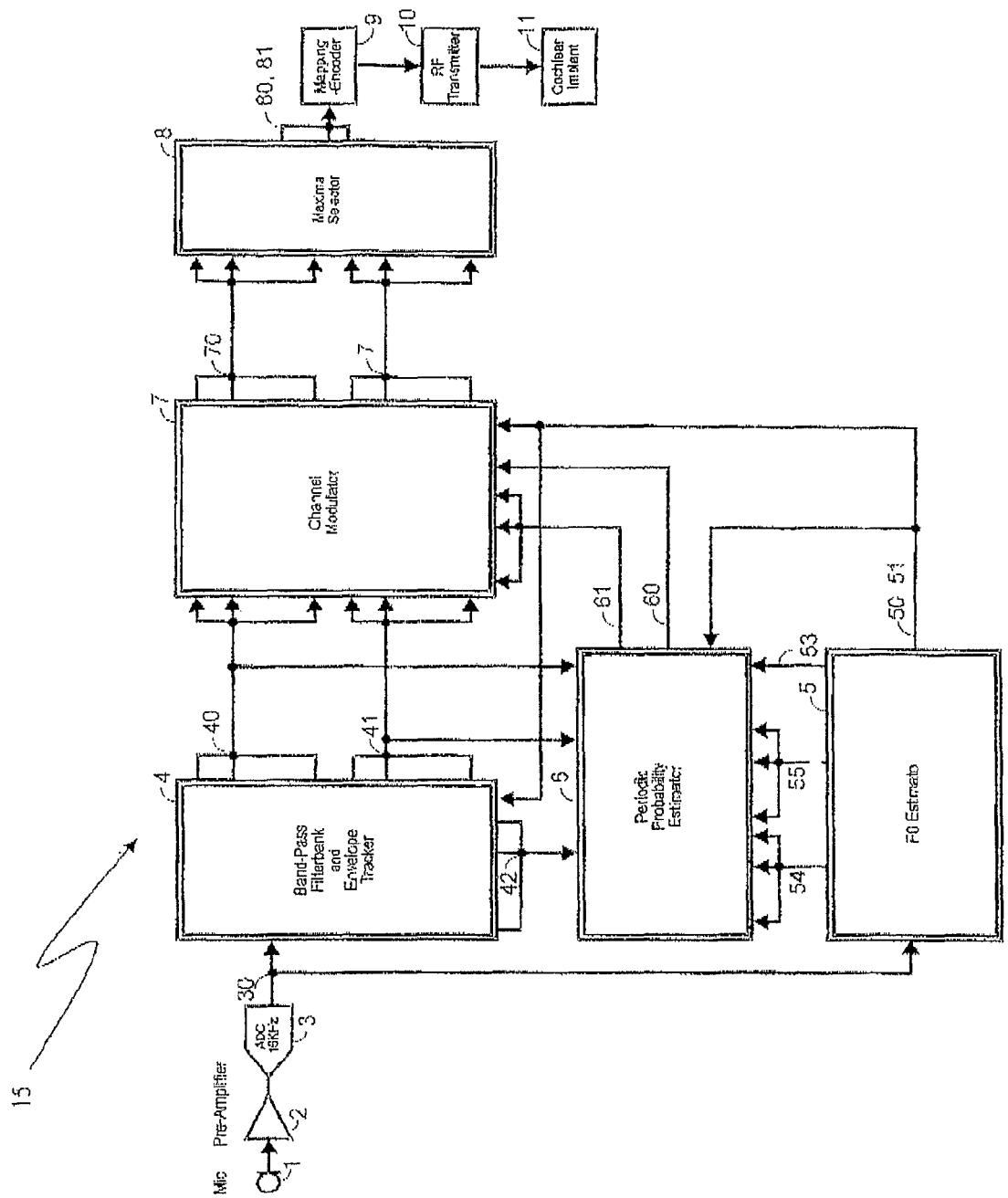
FIG. 2 is a schematic diagram showing various components of a sound processing system in accordance with one embodiment of the present invention.

To address this deficiency, the sound processing system 15 of the present invention is proposed, as is shown in FIG. 2. As described above, the sound processing system 15 of the present invention incorporates some of the basic principles of conventional sound processing systems such as that described above.

In this regard, the sound processing system 15 includes a microphone 1 that converts the acoustic input sound signal into an electrical signal. The resultant electrical signal is then amplified by pre-amplifier 2, and sampled at a rate of 16 kHz using an 8 kHz anti-aliasing low-pass filter followed by an 16-bit analog-to-digital converter 3. The sampled (broadband) signal 30 then passes to the Filterbank 4.

The Filterbank 4 comprises a bank of band-pass filters 43 that process the signal 30 into a plurality of spaced frequency channels (typically $N_{ch}$~20). The Filterbank 4 includes a plurality of envelope estimators or detectors 44 for estimating the envelope of the signal in each spaced frequency channel. A maxima selector 8 is provided to optionally select a subset of the frequency channels based on those with the largest amplitude which are to be further processed for generation of electrical stimulus signals. A mapping-encoder 9 is provided to transform the envelope signals selected by the maxima selector 8 into electrical, stimulus signals in accordance with an individual cochlear implant users' frequency-to-electrode and input intensity-to-electrical stimulation level mapping requirements, as discussed above. An RF transmitter 10 is provided for transmitting the electrical stimulus signals to an implanted cochlear implant receiver-stimulator device 11.

However, unlike the system 20 described above, the system 15 of the present invention is directed to assist in the perception of voice pitch and musical tone in the sound signal. For this reason, the system 15 also includes an F0 estimator 5 that receives the sampled (broadband) signal 30 and estimates, in real-time, the most dominant fundamental frequency (F0) of the signal and the ratio of F0 signal-to-total signal power. A Periodic Probability Estimator (PPE) 6 is also provided to determine the degree to which the signal in each frequency channel, is related to the estimated F0 frequency. To achieve this, the PPE 6 is able to determine whether the signal in each frequency channel contains frequency components, or partials, that are an integer multiple of the estimated F0 frequency, and/or contains periodicity in its' envelope that is equal to the estimated F0 frequency. A channel modulator 7 is also provided as a means of adaptively modulating each channel signals' low-frequency envelope by a periodic function that has a frequency equal to the estimated F0 frequency. As will be apparent below, the system 15 of the present invention also provides a means for adaptively combining (or mixing) the unmodulated (original) channel envelope signals with the modulated channel signals front the channel modulator 7, wherein the gain ratio used to mix these signals is determined by the degree to which the channel signal is related to the estimated F0.

As will become more apparent below, in a preferred embodiment the additional functionality provided by the system 15 of the present invention are primarily implemented in three processing stages, however, a number of minor modifications to some of the standard processing stages are also required.

Figure 3:
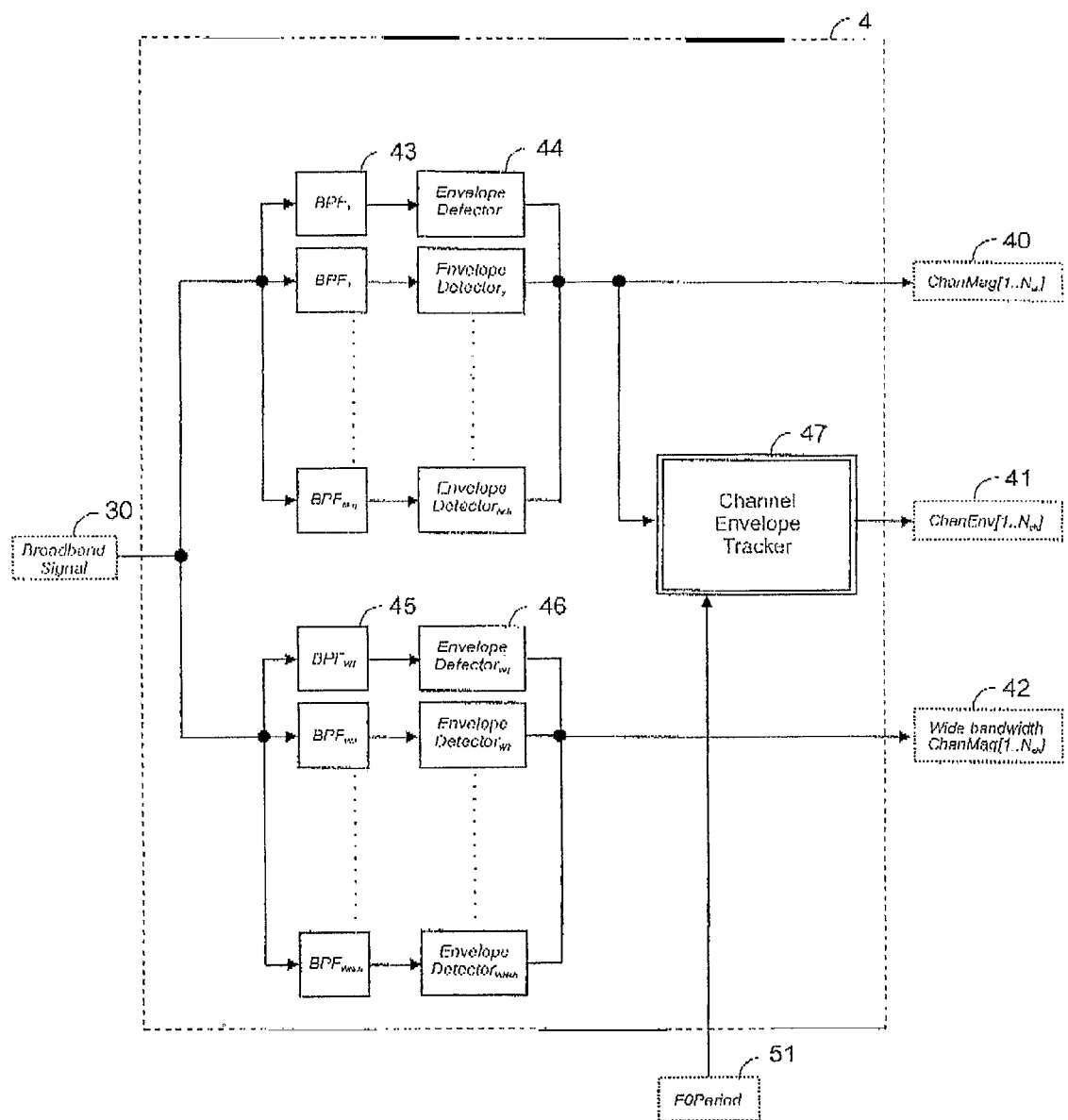
FIG. 3 is a schematic diagram showing one embodiment of the various components of a Band Pass Filterbank and Envelope Tracker in accordance with the system of the present invention.

Referring to FIG. 3, the Filterbank 4 is shown in more detail. The Filterbank 4 employs a first bank of baud-pass filters 43 (implemented using an overlap-add process and a 128-point FFT) in which complex addition of FFT bin vectors is used to construct the channel signals thereby filtering the sampled signal 30 into a plurality of channel signals. The channel signals then pass through a first bank of envelope detectors 44 (implemented via quadrature rectification of the complex channel signals in which the square-root of the sum of squared real and imaginary values are calculated) to produce a set of first channel outputs, referred to as the channel envelope signals 40 (ChanMag). The channel envelope signals 40 are further smoothed in time by the channel envelope tracker 47 to produce a set of second channel outputs, referred to herein as the slow-varying channel envelope signals 41 (ChanEnv).

Figure 4:
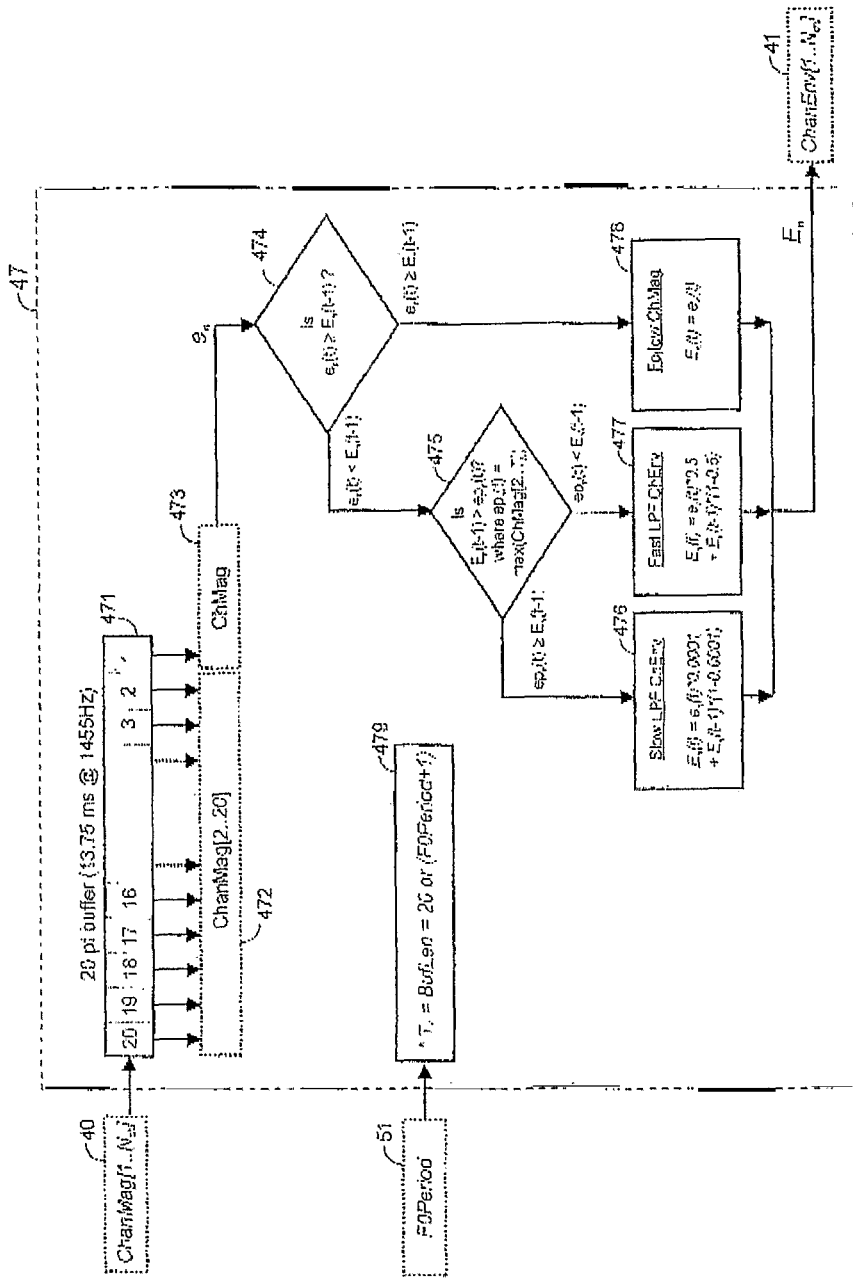
FIG. 4 is a schematic diagram showing one embodiment of the various components of an Envelope Tracker of FIG. 3.

The envelope tracker 47 is shown in more detail in FIG. 4. The envelope tracker 47 is configured to follow the peak level of the envelope signal and to remove modulations above approximately 70 Hz (1455 Hz/20 samples). This is achieved by the envelope tracker 47 receiving each of the channel envelope signals 40 and tracking the magnitudes of each signal. The envelop tracker has an instantaneous attack/time 474 so that it follows all peak levels 478 in the channel envelope signal 40 ChanMag. Upon detecting a peak 475, it holds the peak level (or uses a very slow release time 0.02 Hz, $1^{st}$ order LPF) 476 for a period of up to 20 samples (~13.75 ms) as defined in step 479 (or for a period slightly longer than the estimated F0 period 51) so as to smooth envelope frequency components above approximately 70 Hz (or above the F0 frequency). If a larger signal is encountered during the hold time, the hold lime is reset, otherwise when the hold time expires a rapid release time 477 (300 Hz, LPF) is applied so that envelope components below approximately 70 Hz (or the estimated F0 frequency) are followed. Note, the envelope tracker introduces an additional processing delay of 13.75 ms in the signal path.

Referring again to FIG. 3, the Filterbank 4 is also used to filter the sampled signal 30 using a second bank, of band-pass fillers 45 (also implemented using the same overlap-add 128-point FFT that was used to derive the channel envelope signals) to determine the wide bandwidth channel envelope signals Wide Bandwidth ChanMag 42. Those signals are to be used by the Periodic Probability Estimator (PPE) to determine the probability that, the channel signal is related to the estimated F0. The second bank of band-pass filters 45 are in parallel to the first bank of band-pass filters 43 and are only used for channel frequencies above MaxF (approximately 2 kHz). They have the same centre frequencies as the original bank of band-puss filters 43 used to derive the channel envelope signals 40 and 41, and have a minimum bandwidth that is sufficiently wide so as to pass at least two F0 harmonics of the highest F0 frequency to be analysed by the system (i.e., at least approx 660 Hz wide for a maximum F0 of around 330 Hz). A second set or envelope estimators 46 are used to derive a set of third channel outputs, referred to herein, as the widebandwidth channel envelope signals 42 (Wide Bandwidth ChanMag). Thus, for complex harmonic tones, these channels will carry amplitude modulation in their envelope related to the fundamental frequency of the tone.

The Filterbank analysis rate (or FFT window overlap) is adjustable between rates of approximately 1 ms to 0.5 ms (or 87.5% to 93.75% window overlap) depending on the electrical stimulation rate desired. Typically, a rate of 0.6873 ms (i.e., 16000 Hz/11 samples=1455 Hz) is employed which is sufficiently high enough to sample F0 frequencies up to approximately 360 Hz.

As alluded to above, The F0 Estimator 5 is used to derive a real-time estimate of the fundamental frequency 50 (F0Freq) that pertains to the most dominant harmonic signal, if any, present in the input sound signal 30. It also provides an estimate of the harmonic signal-to-total signal power ratio, or alternatively described as the F0 Signal-to-Noise+Signal power ratio 53 (F0SNSR), hi achieving this, the F0 Estimator 5 incorporates a number of processing stages. The first stage is used to estimate the power and frequency of components in the input signal. In the second stage, a series of harmonic sieves, where each sieve passes harmonics of a given F0, is used to determine the amount of power present (or matched) in the signal that pertains to the given (candidate) F0. A range of F0 frequencies, separated by one semitone, are examined and the candidate F0s that pass the highest amount of power are found. In the third stage; for candidate F0s with the highest matched powers a second bank of harmonic sieves with finer frequency resolution are applied. Stage four is used to reduce F0 octave errors. A weighting function is applied to the matched power of the highest candidate F0s so as to minimize octave errors in quiet and noisy conditions. The candidate F0 with the highest weighted matched power is selected as the F0 estimate for the current time frame of the F0 estimator. The final stage is used to reduce spurious F0 estimation errors in noisy conditions by selecting the best F0 estimate from those obtained over a number of consecutive time frames. A detailed description of each stage follows below.

Figure 5:
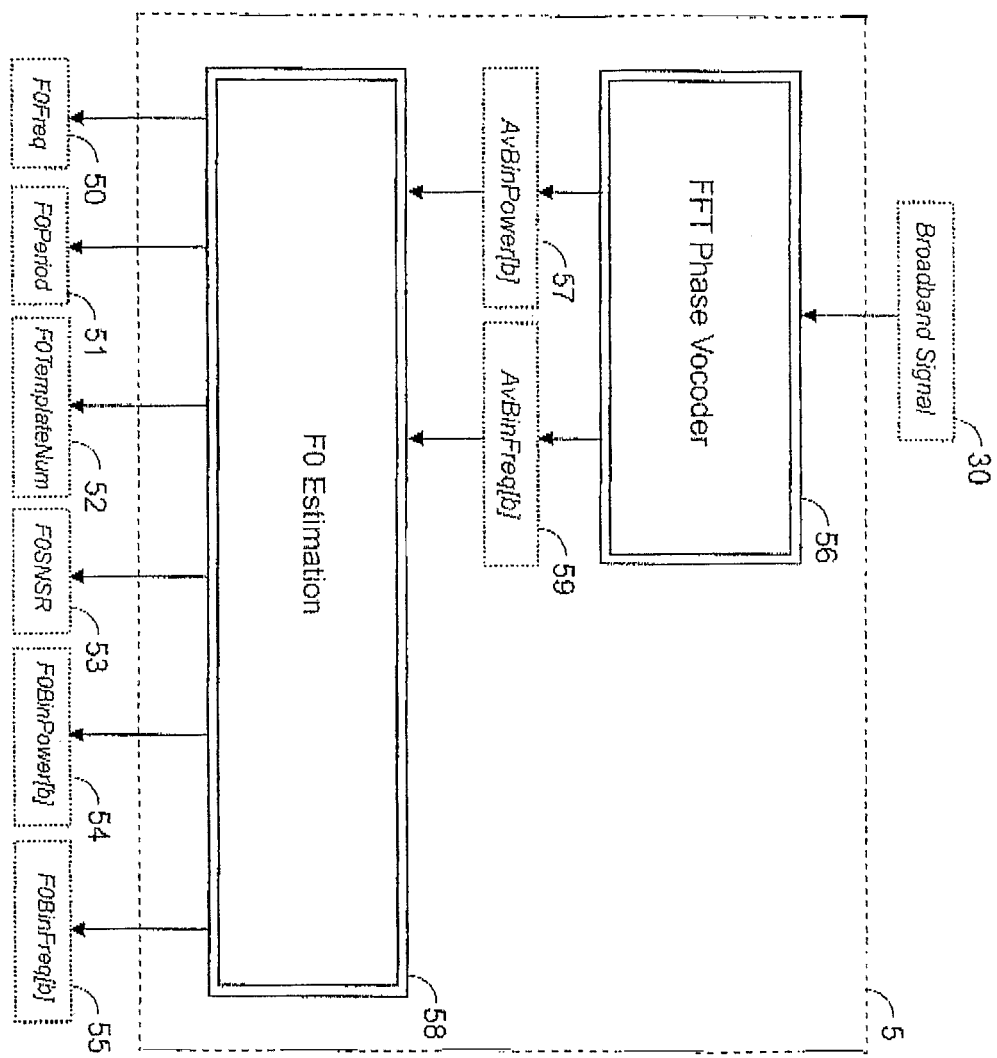
FIG. 5 is a schematic diagram showing one embodiment of the various components of a F0 Estimator in accordance with the system of the present invention.
Figure 6:
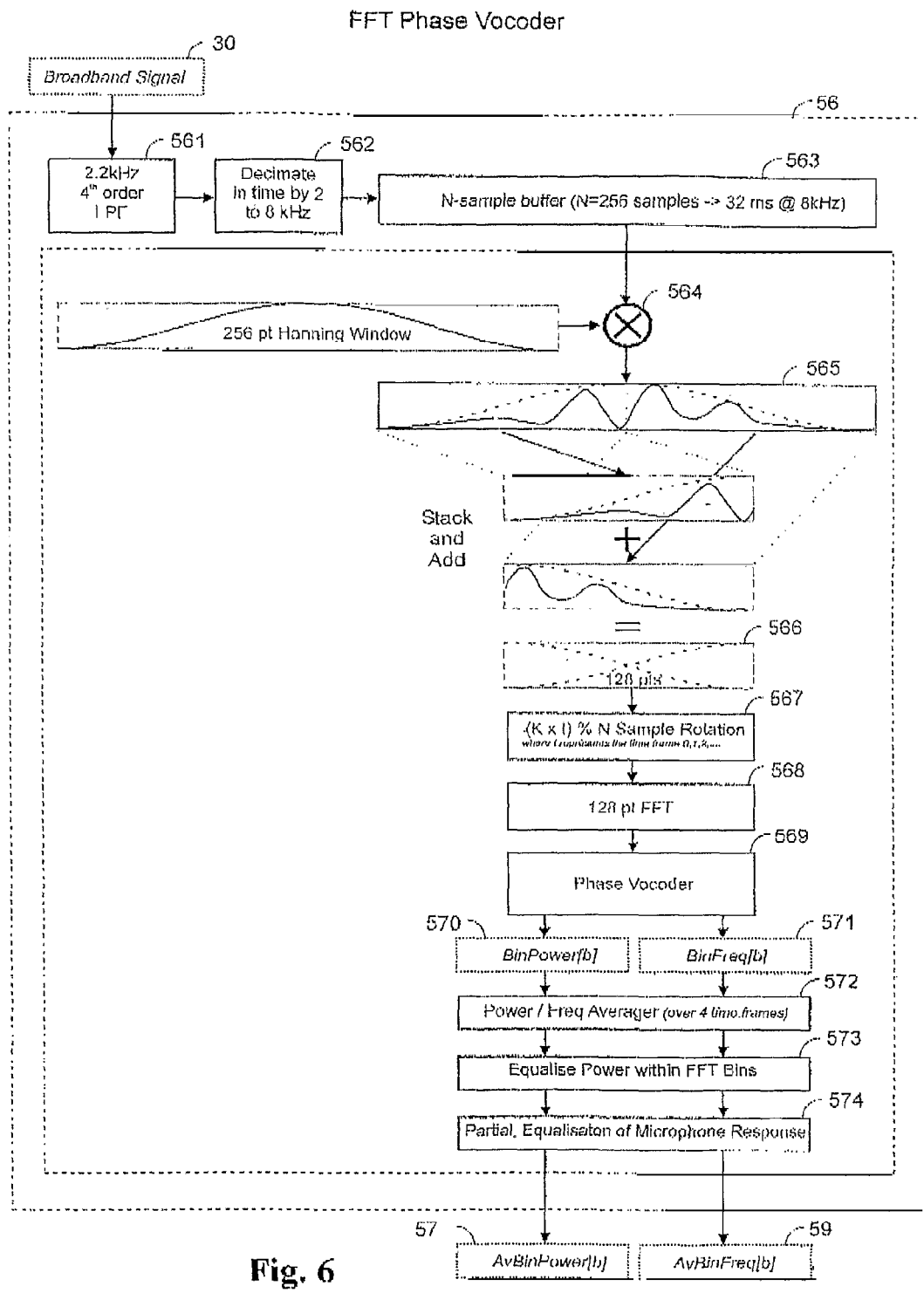
FIG. 6 is a schematic diagram showing one embodiment of the various components of a FFT Phase Vocoder of the F0 Estimator of FIG. 5.
Figure 7:
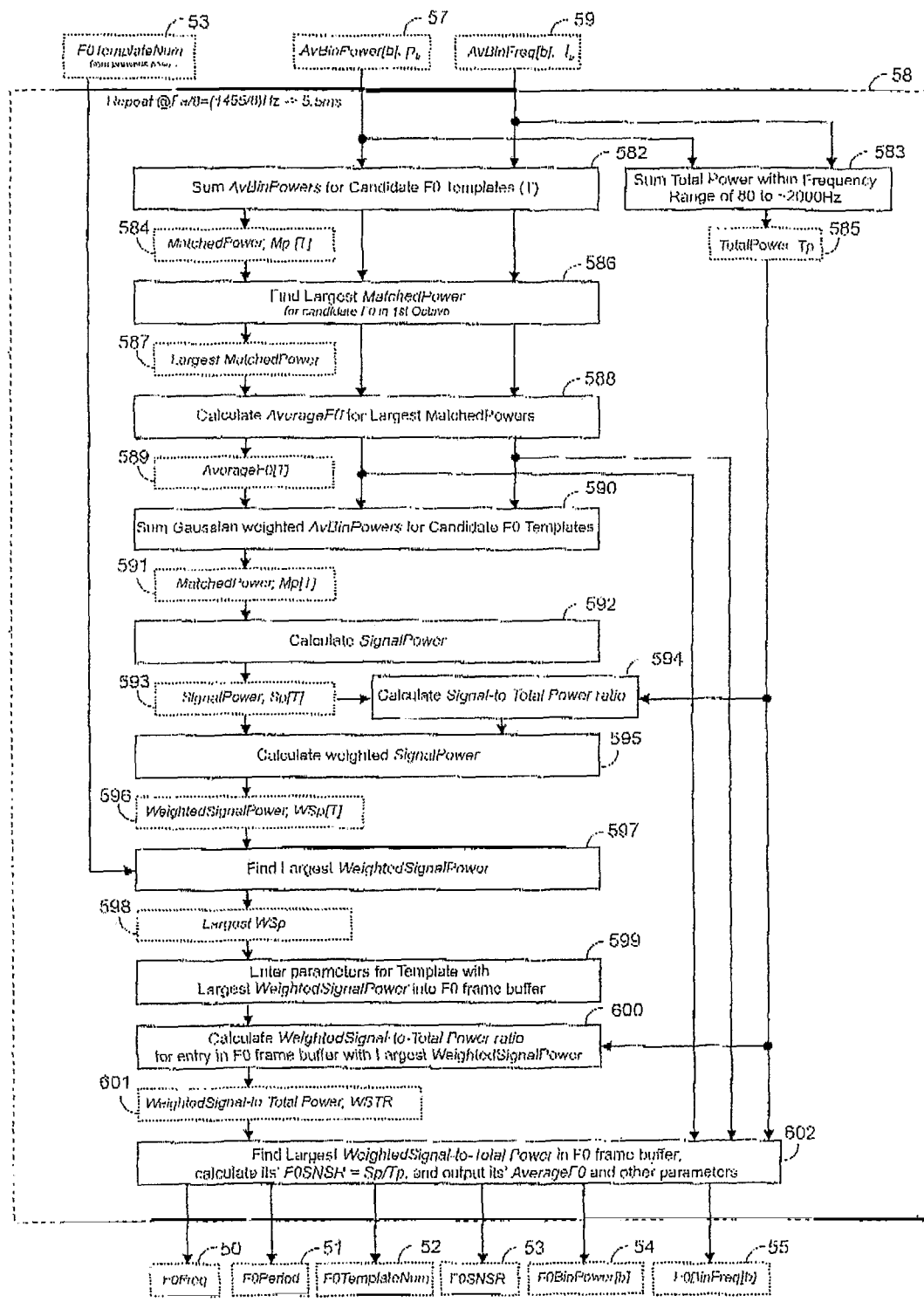
FIG. 7 is a flow chart showing one embodiment of a process undertaken by the F0 Estimator of FIG. 5 to generate values associated with the fundamental frequency of the input sound signal
Figure 8:
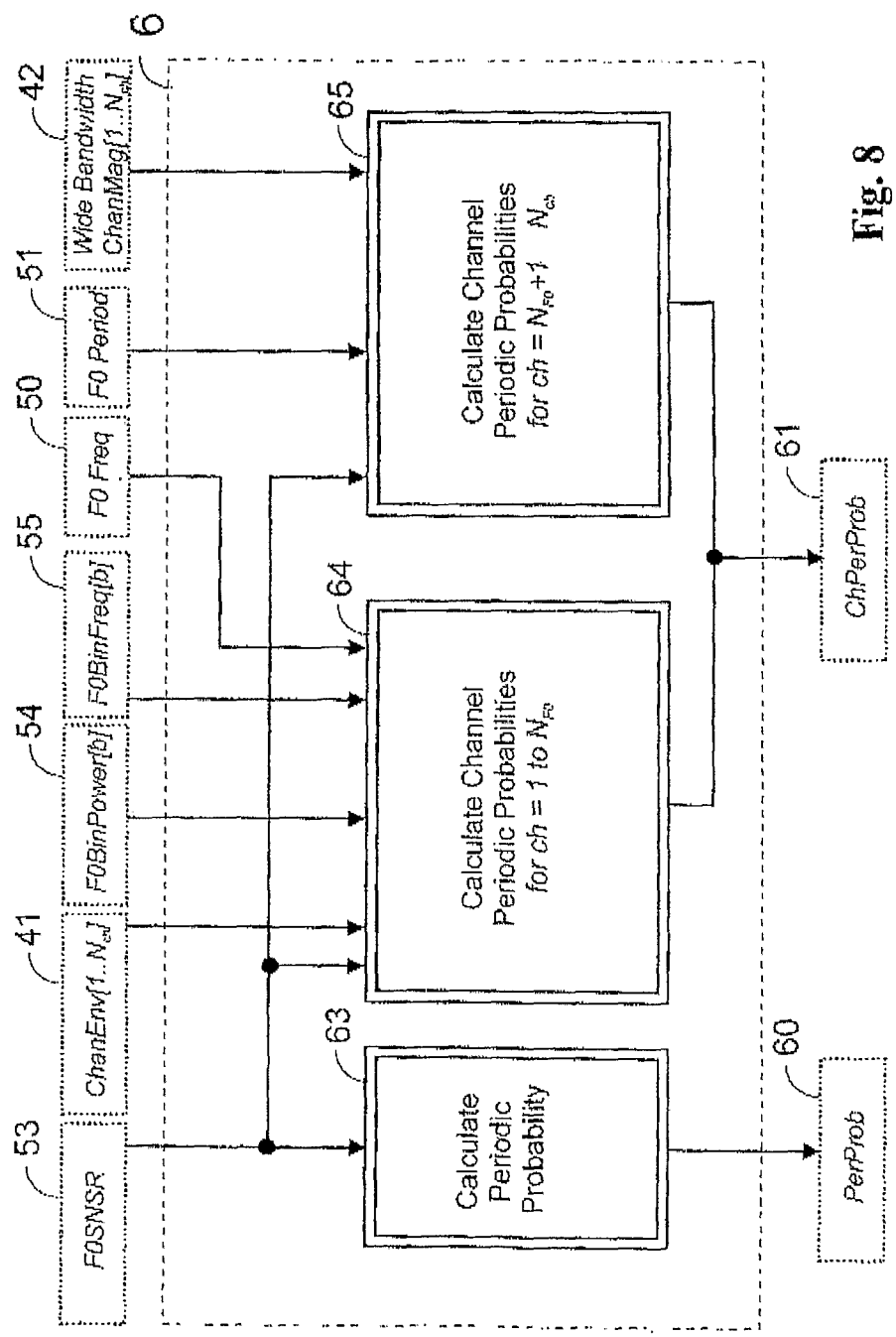
FIG. 8 is a schematic diagram showing one embodiment of the various components of a Periodic Probability Estimator in accordance with the system of the present invention.

Referring to FIGS. 5-7, the first stage of the F0 Estimator 5 is depicted. This stage utilises a Fast Fourier Transform (FFT) phase vocoder 56 to provide estimates of the frequency or power of sinusoidal components (or partials) present in the input signal 30.

The manner in which the FFT Phase Vocoder 56 functions is shown in detail in FIG. 6. In step 561 the sampled signal 30 typically received from a microphone worn by a cochlear implant recipient, is initially low-pass filtered using a low-pass anti-aliasing filter ($4^{th}$ order, infinite-impulse-response (IIR) butterworth filter with a 2.2 kHz cut-off frequency) prior to down-sampling (decimation in time by a factor of 2) to a rate of 8 kHz at step 562. In step 563, the most recent 32 ms, i.e., 256 samples, of the down-sampled signal are then windowed in step 564 using a Hanning window (which provides a −3 dB bandwidth of 31.25 Hz in the frequency domain). A "stacking and adding" technique is then performed in step 565, which is used to reduce the number of samples to 128 (at step 566) via decimation in the frequency domain by a factor of 2.

In step 567, these samples are rotated in time by −(k×t) samples, where t is the analysis frame number (t=0, 1, 2, . . . ), k=analysis frame rate=11 samples (which provides an analysis frequency=8000 Hz/11-727 Hz), and N×128 samples. The rotation is performed so as to maintain a zero relative phase shift between successive FFT frames for the phase vocoder processing that is to follow. At step 568, a 128-point FFT is then applied to obtain an estimate of the input signals' complex frequency spectrum where FFT bins b=1 to 32, represents frequency bands spaced by 62.5 Hz having centre frequencies in the range of 62.5 to 2000 Hz.

At step 569, a phase-vocoder is then used to estimate the bin power values 570 and bin frequency values 571 of signal components within FFT bins 1 to 32. Bin power values are derived from the sum of squared real and imaginary FFT values, whilst bin frequency values are estimated from the phase difference between successive FFT frames. This is done by calculating the phase (Ph) from the real and imaginary terms in each FFT bin (where Ph=arctan(imaginary/real)) and using the phase difference (dPh) between successive FFT frames to calculate the bin frequencies (where the bin frequency b×Fs/N+dPh[b]×Fs/(k×2π), and b=FFT bin number, k=analysis hop=11 samples, Fs=8000 Hz, and N=128 samples). Note, the calculated phase differences are "unwrapped" prior to calculating the bin frequency. The bin powers and bin frequencies are then arithmetically averaged over 4 FFT frames in step 572 to produce the average bin power 57 (AvBinPower[b] or $p_b$) and average bin frequency 59 (AvBinFreq[b] or $f_b$) values for FFT bins b=1 to 32. Through averaging the bin powers and bin frequencies over four successive frames, average terms are produced every 5.5 ms (182 Hz). The average bin power for each bin is calculated using AvBinPower·(P1+P2+P3+P4)×0.25, where P1 to P4 are the FFT bin powers for four successive FFT frames. The average bin frequency for each bin is calculated using AvBinFreq=(F1×P1+F2×P2+F3×P3+F4×P4)/(P1+P2+P3+P4), where F1 to F4 are the FFT bin frequencies for four successive FFT frames. Because the bin powers and bin frequencies are averaged over 4 successive FFT frames (FFT frame rate=8000 Hz/11 samples=727 Hz), the remainder of processing within the F0 estimator is carried at a rate of 727/4=182 Hz. The allowable upper value for average bin frequencies is MaxF=(32+0.5) FFT bins×62.5 Hz (bin-width)−2.031 kHz. Average bin powers with frequencies beyond this limit are set to zero.

The average bin powers 57 values can be optionally modified so as to account for excessive ripple in composite spectral magnitude response of the processed signal 566 which was windowed by a 256 point Hanning window and decimated in frequency by 2 in step 505. The frequency decimation process effectively introduces greater attenuation in frequency components that are off-centre of the FFT bin centre frequency than would normally be the case if no frequency decimation occurred. Thus, in step 573, the composite magnitude response of the system can be flattened by applying the inverse magnitude response, of the window (for bin frequencies within +/− half the bin width from the centre frequency of the bin) to the average bin powers based on their average bin frequency.

For input signals obtained from the microphone 1, the average bin powers 57 are also equalised in step 574 across the frequency range of 0-2 kHz by a function proportional to the inverse of the microphones spectral magnitude response. The function has a −4 dB/octave response from 62 Hz to 2 kHz. For input signals fed directly into the system (i.e., bypassing the microphone), equalisation of the average bin powers is bypassed.

Referring again to FIG. 5, having derived the average bin powers 57 mid the average bin frequencies 59, these are then used in the second stage of the F0 Estimator to carry out the F0 Estimation process 58.

The F0 estimation process is described in more detail with regard to FIG. 7. Firstly, the amount of power in the sampled input signal 30, below 2 kHz, that is harmonically related to a candidate F0 frequency is determined. This is done for candidate F0 frequencies starting from approximately 82 Hz increasing up to approximately 329 Hz (or higher e.g., up to 523 Hz depending on system parameters) in steps of 1 semitone, or ~5.94% (i.e., 82, 87, 93, 98, 104, 110, . . . , 311, 329 Hz) which correspond to notes E2 to E4 on a western musical scale. For each candidate F0 frequency the summed or matched power is determined in step 582 by summing average bin powers 57 if their average bin frequency 59 falls within a series of rectangular harmonic sieves (i.e. ideal BPFs) centred at multiples of the candidate F0 frequency as given by the frequency set:

$$F_r[T] = \{f : f \geq 2^{-0.5/12} nC_{F0} - F_{offset} \text{ and } f \leq 2^{+0.5/12} nC_{F0} + F_{offset}\}$$

for T=1 to 28 and n=1, 2, 3 . . . .

Where: T is the candidate F0 template number; $C_{F0}$ is the candidate F0 frequency=$82 \times 2^{T/12}$; $F_r[T]$ are the sieve frequency ranges that span +/−0.5 semitones around all integer multiples (n) of $C_{F0}$ up to a maximum harmonic frequency of MaxF; and $F_{offset}$=2 Hz which is used to provide a small amount of overlap between sieves of adjacent candidate F0s.

The matched power is then calculated in step 582 for each candidate F0 frequency using the FOLLOWING equation;

$$Mp[T] = \sum_{b}^{\forall b : f_b \in F_r[T]} p_b$$

Prior to summing the average bin powers for each candidate F0 in step 582, an additional rule can optionally be employed. For each candidate F0, the largest average bin power value that falls within the range of frequencies to be summed is first determined. This value is used to establish a threshold for summation of the average bin power values. The threshold is typically set to 0.001× largest average bin power for "quiet conditions" or 0.01× largest average bin power for "noisy conditions". Average bin powers that fall below this threshold are not summed in step 582. "Quiet conditions" and "noisy conditions" are approximately delineated by signal-to-noise ratios (SNRs) of greater than +6 dB and less than 16 dB respectively. In the present implementation the selection of "quiet condition" or "noisy condition" parameters is made by the user. Future implementations could adaptively control selection of parameters based on an estimate of SNR.

In the third stage, under ideal conditions, the candidate F0s with the largest matched powers could be used to derive an estimate of F0. However, in order to determine F0 estimates that are more robust to the effects of noise, a second harmonic sieve process is employed which uses narrower sieves centred at multiples of average F0 frequencies derived from the harmonics summed in stage 2 above. In addition, to reduce processing requirements, the remaining processing stages 3 to 5 are only performed for candidate F0s with matched powers with in 3 dB power (i.e., 0.5) of the largest matched power 587 derived from step 586 and for those in which at least two average bin power values (or harmonics) were summed to provide the matched power.

The average F0 frequencies 589 (AverageF0) are calculated in stop 588 from the power-weighted mean of bin frequencies $f_b$ which fall within the range of frequencies summed for the candidate F0 and then dividing by the sum of average bin powers for the same set of bins as per the equation below:

$$AverageF0[T] = \sum_{b}^{\forall b : f_b \in F_r[T]} f_b p_b \Big/ \sum_{b}^{\forall b : f_b \in F_r[T]} p_{b0}$$

The second bank of harmonic sieves are Gaussian in function and are implemented in step 590 to derived the weighted matched power 591. The weighted matched power is calculated by scaling the power of each frequency component that is summed by a Gaussian function G that is proportional to how close the component frequency $f_b$ matches its nearest integer multiple of the average F0 frequency for the given candidate F0. The Gaussian sieves have mean centre frequencies positioned at harmonic multiples of AverageF0 and standard deviations equal to multiples of as given by the equation below: where h is the harmonic number, or nearest integer multiple of AverageF0 closest to the bin frequency $f_b$. The standard deviation $k_G$ is used to establish the bandwidth of Gaussian sieves. Setting $k_G$=0.02×$C_{F0}$, fixes G at ~0.5 (i.e., half power) when the bin frequency divided by the harmonic number $f_b/h$ approximately +/−2.4% (or ~+/−0.4 semitones) away from the AverageF0.

$$G(f_b, AverageF0[T]) = \exp\left(\frac{-(f_b/h - AverageF0[T])^2}{2k_G^2}\right)$$

where h is the harmonic number for $f_b$ with respect to the average F0 which is given by the following equation;

$$h = \lfloor f_b / AverageF0[T] + 0.5 \rfloor$$

For low candidate F0s, higher order harmonic sieves can overlap significantly if $k_G$ set too high. In addition in noisy conditions, the higher order wide sieves can sum a lot of noise power. Thus, the standard deviation of the Gaussian sieves in the equation above were limited such, that $k_G$ could not exceed some maximum value $k_{GMax}(h)$ as defined by the following equation, where the limiting bandwidth $BW_{Max}$ was set to 60 Hz.

$$K_{GMax}(h) = \frac{BW_{Max}}{2h\sqrt{-2\ln(0.5)}}$$

The amount of power 591 passed by the second bunk of harmonic sieves 590, hereafter replacing the matched power derived in step 584 is determined by summing the bin powers weighted by the Gaussian sieves as per the following equation, where $AVF0_r(T)$ are the Gaussian sieve frequency ranges which span 12 semitones around all integer multiples of AverageF0.

$$Mp[T] = \sum_{b}^{\forall b : f_b \in AVF0_r[T]} p_b G(f_b, AverageF0[T])$$

In quiet conditions, the matched power consists entirely of signal power (Sp), however in noisy conditions, the matched power comprises both the signal power and a portion of the noise-power (Np). Thus an optional processing stage can be employed to derive a better estimate of the signal power by subtracting an estimate of the noise power within the sieve from the matched power. Starting from the assumption that the input, signal consists of a mono-phonic complex harmonic-signal and noise distributed uniformly across the 2 kHz, frequency range, it can be shown that, for the candidate F0 corresponding to the F0 signal, the noise power (Np) within the matched bandwidth is equal to total power (Tp) minus the matched power multiplied by the matched bandwidth-to-total bandwidth ratio, i.e., $Np=(Tp-Mp) \times K_{BW} \times M_{BW}/T_{BW}$, where the total bandwidth $T_{BW}=MaxF-60$ Hz, the total power 585 (Tp) is derived from the summation of all bin powers with bin frequencies within the total bandwidth 583, and the matched bandwidth was calculated by summing the bandwidth of each Gaussian sieve as per the following equation where a –3 dB (0.5) power bandwidth for each Gaussian sieve is assumed.

$$M_{BW}[T] = \sum_{h}^{h>T_{BW}/C_{F0}} 2hk_G\sqrt{-2\ln(0.5)}$$

Next, given that the matched power comprises both the signal power and noise power within the matched bandwidth, i.e., Mp=Sp+Np, the signal power (Sp) 593 is derived in step 592 by transposition of the above equations to give the equation below;

$$Sp[T] = \frac{Mp[T] - Tp \cdot K_{BW}\left(\frac{M_{BW}[T]}{T_{BW}}\right)}{1 - K_{BW}\left(\frac{M_{BW}[T]}{T_{BW}}\right)}$$

The constant $K_{BW}$ is used to compensate for the fact that signal and noise are typically not uniformly distributed across the frequency range. Experimentation with $K_{BW}$ found that a value of 0.5 provided a good compromise between noise power estimates for different signals, noise types, and SNRs.

The fourth stage of the process comprises minimising octave errors. For harmonic sieve based estimators, octave errors arise because harmonics of F0 align with even numbered harmonics of submultiples of F0 (i.e., lower octaves of F0). Thus in the present implementation, equal, signal powers (or alternatively if step 592 is bypassed, equal matched powers) are derived for candidate F0s corresponding to the signal F0 and all lower octaves of F0 thereby introducing F0 errors in which a lower octavo of F0 (sub-octavo error) results. This problem is counteracted by applying a small amount of positive weighting to the signal power (or matched power) of higher candidate F0s. However, too much positive weighting can introduce errors in which a higher octave F0 is estimated for eases where the amount of energy in odd numbered harmonics of F0 is low compared to that of even numbered harmonics. Thus, careful choice or the weighting function is required so as to minimize both the sub-octave and higher-octave type errors. To further complicate mailers, the choice of weighting function will be dependant on signal-to-noise ratio. As noise is introduced, lower candidate F0s sum more noise than higher candidate F0s (because they have more harmonic sieves) and thus greater positive weighting is needed for higher candidate F0s to counteract sub-octave F0 errors.

In the present implementation, positive weighting is applied to higher candidate F0s. The weighting function compensates for differences in the combined bandwidth of all harmonic sieves summed for each candidate F0s. It is inversely proportional to the matched bandwidth $M_{BW}$ (i.e., the bandwidth of all harmonies sieves summed) raised to the power $K_W$ as given by the following equation: where the constant $K_W$ is used to adjust the degree of positive weighting.

$$W[T]=M_{BW}[T]^{-K_W}$$

The weighted signal power 596 is derived in step 595 from $WSp[T]=Sp[T] \times W[T]$ (or alternatively if step 592 is bypassed the weighted matched power can be derived from $WMp[T]=Mp[T] \times W[T]$). Through experimentation using a range of speech signals and F0s presented in quite conditions, the best F0 estimation accuracy was determined for $K_W$–0.02 to 0.1. However when, noise was added to the signal, higher values of $K_W$–0.20 to 0.34 were required to compensate for the increase in noise power summed by low candidate F0s. For high-to-moderate SNRs (i.e., greater than approximately 1-6 dB) "quiet condition" processing parameters are employed (i.e., $K_W$–0.08), for lower SNRs, "noisy condition" processing parameters are employed (i.e. $K_W$–0.3). Au algorithm for adaptive adjustment of $K_W$ was also examined. An estimate of signal-to-total power ratio STR for the largest weighted power is calculated in step 594 using STR=Sp/Tp (or alternatively STR=Mp/Tp). The STR value ranged from 1.0 corresponding to a high SNR, through to ~0.5 or lower corresponding to SNRs of 0 dB and lower. The adaptive algorithm linearly adjusted $K_W$ between values of 0.02 to 0.34 for STR values ranging from 1.0 to 0.55 using the following equation: $K_W$–(0.02–0.34)×(STR–0.55)/(1.0–0.55)+0.34. For STR values less than 0.55, $K_W$ was limited to 0.34.

The candidate F0 with highest weighted signal power 598 (or alternatively the highest weighted matched power) is determined in step 597 and its' average F0 is used as the F0 estimate for the current frame of the F0 estimator.

In step 597, an optional method of octave error reduction can be employed which compares the current F0 estimate with, that from the previous F0 Estimator frame 53 anil applies some hysteresis if the two F0 frequencies are related by a integer, or near integer ratio (e.g., if the previous F0 estimate=110 Hz and the current F0 estimate=326 Hz which is 2.96 times higher in frequency, then hysteresis is applied). Note, this is actually carried out using F0 template numbers (T), rather than the F0 frequency, allowing a tolerance of +/–1 templates. Integer frequency ratios exist for template number differences of 12, 19, 24, 28, and 30 (i.e., ×2, ×3, ×4, ×5, and ×6 respectively). If the templates are harmonically related and the current weighted signal power×hysteresis threshold is less than the previous weighted signal power, then the previous F0 estimate is retained (i.e., it overrides the current F0 estimate) where the hysteresis threshold typically is 0.98 for "quiet conditions", or 0.9 for "noisy conditions".

In stage 5, it has been found that in noisy conditions, spurious fluctuations in the weighted signal power (or weighted matched power) introduce estimation errors and thus a final processing stage is included which selects the best F0 estimate from a number of consecutive F0 estimator frames (i.e., similar to a process of listening in the gaps). In step 599, parameters (i.e., T, WSp, AverageF0, AvBinPowers, and AvBinFreqs) for the candidate F0 with the highest weighted signal power (or weighted matched power) are entered into the F0 frame buffer. In addition, in stop 600 the largest weighted signal power (or weighted matched power) is normalised by the total power 585 to provide an estimate of the weighted signal power-to-total power ratio 601 WSTR WSp/Tp (or alternatively WSTR=WMp/Tp). The entry in the Ft) frame buffer with largest. WSTR is used for selection of the best F0 estimate across consecutive frames in step 602. It was found that the number of consecutive frames for selection of the best F0 estimation in "quiet conditions" is around 4 (which covers a time range of ~20 ms), whereas for "noisy conditions" best results were obtained by using a greater number of frames, for example, up to 12 frames (i.e., 60 ms). Upon determination of the frame with the best F0 estimate, its' average F0 is output by the F0 estimator as F0Freq 50. The F0 period 51 (F0Period) in units of samples (using a sampling rate of 8000/11=1455 Hz) and its candidate F0 template number T 52 (F0TemplateNum) are also output. In addition, an estimate of the "unweighted" signal-to-total power ratio, F0SNSR=Sp/Tp (or alternatively F0SNR Mp/Tp) is output by the F0 estimator 53. This value is used in later stages of the present invention as a measure of the F0 estimation strength, or the probability that the signal (within the 0-2 kHz range) is harmonic. Finally, FFT bin power 54 (F0BinPower[b]) and frequency 55 (F0BinFreq[b]) values for the best F0 estimator frame are output (64 and 65 respectively) for use by the periodic probability estimator stage.

Referring to FIGS. 8-11, the Periodic Probability Estimator (PPE) 6 is shown in detail. A component 63 of the PPE 6 is used to estimate the probability that the input signal 30 consists of two or more harmonically related sinusoidal components (or partials), i.e. that it is "periodic" (with the exclusion of pure-tones). The PPE generates an input signal. Periodic Probability value 60 (PerProb) derived from the F0SNSR value 53 (i.e., the ratio of harmonic signal-to-total signal power) which is derived from the F0 Estimator 5.

Figure 9:
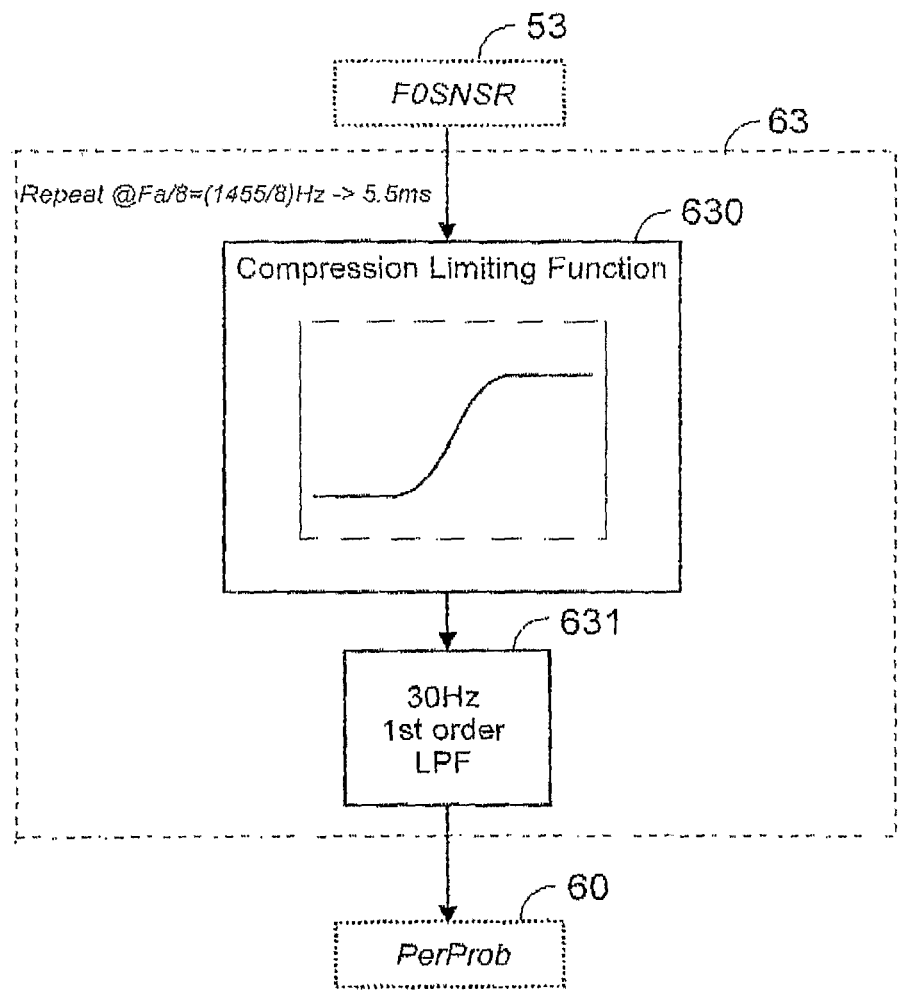
FIG. 9 is a flow chart showing one embodiment of the process undertaken by the Periodic Probability Estimator of FIG. 8 to estimate the probability that the input signal received by the system is harmonic (or periodic)

Referring to FIG. 9, the F0SNSR value 53 is initially transformed using a compression-limiting function 630 into a range appropriate for categorising the signal as periodic (harmonic)=1.0 or non-periodic=0.0. The maximum F0SNSR value is 1.0 for the case when the input is comprised entirely of a complex-harmonic signal and it approaches 0.0 for the case when the input contains no periodicity whatsoever. The non-linear compression-limiting function 630 (as described by the sigmoid function in the equation below where a is the inflection point and b sets the 5%-95% width of the function) is used to transform the F0SNSR value into a range appropriate for categorising the signal as "periodic" or "non-periodic".

$$PerProb(F0SNSR) = \frac{1.0}{1.0 + \exp(-6.0 \times (F0SNSR - a)/b)}$$

for "quiet conditions" the sigmoid function has an inflection point a=0.65, and a width b=0.4. For "noisy conditions" the function has an inflection point a=0.575, is and width b=0.35. The transformed F0SNSR value is then passed through a low-pass filter 631, using a $1^{st}$ order 30 Hz LPF, to smooth out any spurious fluctuations in the output Periodic Probability value 60 (PerProb).

The Periodic Probability Estimator 6 is also used to estimate the probability that the signal in any frequency channel is related to the estimated F0 frequency (i.e., contains frequency components, or partials, that are an integer multiple of the estimated F0 frequency, and/or contains periodicity in its envelope that is equal to the estimated F0 frequency). This is carried out using two methods. The first method 64 is used for low frequency channels, typically those in the range 0-2 kHz. The second method 65 is used for higher frequency channels, typically those above 2 kHz.

Figure 10:
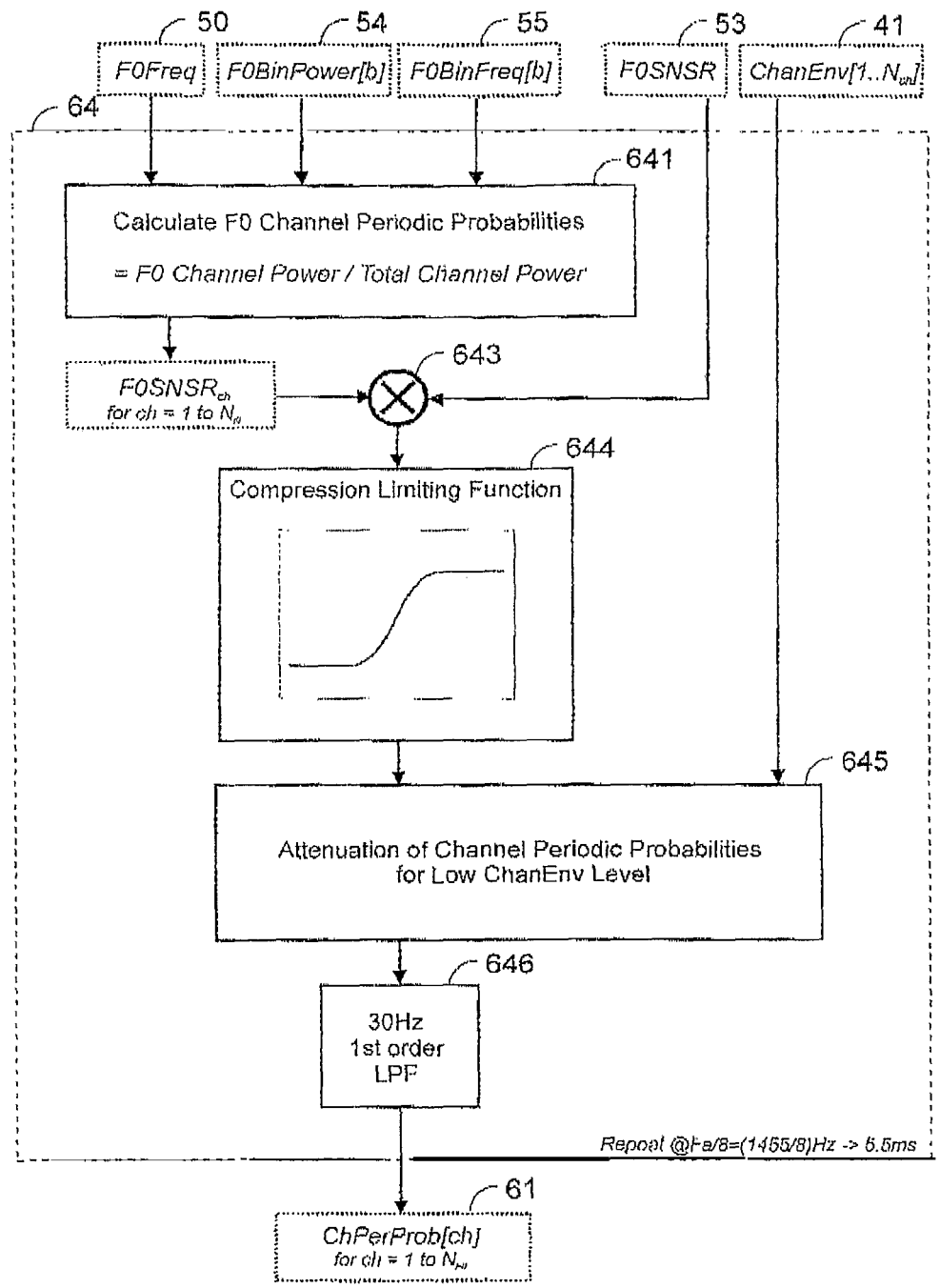
FIG. 10 is a further flow chart showing one embodiment of the process undertaken by the Periodic Probability Estimator of FIG. 8 to estimate the channel periodic probability for each channel that has a centre frequency less than or equal to 2 kHz.

The manner in which the method 64 of the PPE 6 achieves this is shown in FIG. 10. For frequency channels that fall within the range of F0s' analysed by the F0 Estimator (typically 0-2 kHz), the channel periodic probability 61 (ChPerProb) or the probability that the channel signal contains sinusoidal components, or partials, that are an integer multiple of the estimated F0 is determined using a function of the signal power within the BPF channel that is related to the estimated F0 divided by the total signal power within the channel. This ratio, i.e., the channel power-to-total power F0SNSR$_{ch}$, is estimated as per the following equation for channels n=1 to 11 typically for N$_{ch}$=20 channel filterbank.

$$F0SNSR_{ch}[n] = \frac{\sum_{\forall b: F0BinFreq[b] \in F_{ch}[n]} F0BinPower[b] G(F0BinFreq[b], F0Freq) P_{ch}(F0BinFreq[b])}{\sum_{\forall b: F0BinFreq[b] \in F_{ch}[n]} F0BinPower[b] P_{ch}(F0BinFreq[b])}$$

The F0 signal power and total power within each BPF channel is derived from the bin powers (F0BinPower[b]) and frequencies (F0BinFreq[b]) obtained from the F0 Estimator that correspond to the current F0 estimate. For each BPF channel which spans a frequency range denoted F$_{ch}$ (as per the −60 dB power bandwidth of the BPF), the signal power within the channel is estimated by firstly weighting all bin powers within the range F$_{ch}$, according to how closely their frequency matches that of harmonics of the estimated F0. The weighting factor is derived from the Gaussian function described above in relation to the third stage of the F0 Estimator where k$_G$=F0Freq and BW$_{Max}$=30 Hz. This results in 30 Hz wide Gaussian fillers for all harmonics and F0s. (Note, k$_G$ can be reduced as low as 0.1×F0Freq so as to reduce the Gaussian filter width for low-order harmonics and thereby provide greater accuracy in the channel periodic (harmonic) probability). Next, the weighted bin powers are scaled by the power response of the BPF channel P$_{ch}$(f) for each bin frequency and summed to provide an estimate of the F0 signal power within the channel, as per the numerator in the equation above, step 641.

The total power in the BPF channel is derived from the summation of bin powers scaled by the power response of the channel at each bin frequency as shown in the denominator of the equation above. At step 643, the channel F0SNSR$_{ch}$ is normalized (i.e., multiplied) by the 0-2 kHz signal power-to-total power ratio F0SNSR (which reflects the probability that the overall signal is harmonically related to the estimated F0). The resultant value ranges from approximately 1 when the channel signal contains frequency components related to the estimated F0 and the F0SNSR is high, down to approximately 0 when the channel signal is not related to the estimated F0 and F0SNSR is low. A channel periodic probability value is then determined 644 by transforming the scaled F0SNSR$_{ch}$ value using a sigmoidal function as per the following equation, where a=0.5 sets the inflection point, and b=0.5 sets the ~5%-95% width of the sigmoid function. This function returns channel periodic probabilities approaching 1 for scaled F0SNSR$_{ch}$ values of 0.75 or higher, 0 for scaled F0SNSR$_{ch}$ values of 0.25 or lower, and values between 1 and 0 for scaled F0SNSR$_{ch}$ values between 0.75 and 0.25.

$$ChanPerProb[n] = \frac{1.0}{1.0 + \exp(-6.0 \times (F0SNSR \times F0SNSR_{ch}[n] - a)/b)}$$

An additional adjustment, is made to reduce the channel periodic probability value, and hence reduce the depth of F0 modulation applied later by the Channel Modulation stage, when the channel signal level is low. This is done to minimize reductions in the loudness elicited by low intensity channel signals. To achieve this, the channel periodic probability is attenuated in step 645 when the slow-varying channel envelope signal ChanEnv is within the lower 16 dB of the 40 dB input dynamic range of the channel. The amount of attenuation ranges from 1.0, for ChanEnv equal to 16 dB re the minimum channel level, linearly down to 0.25 for ChanEnv equal to the minimum channel level. As a final stage 646 the channel periodic probability value is filtered using a 30 Hz $1^{st}$ order LPF to smooth spurious fluctuations.

Figure 11:
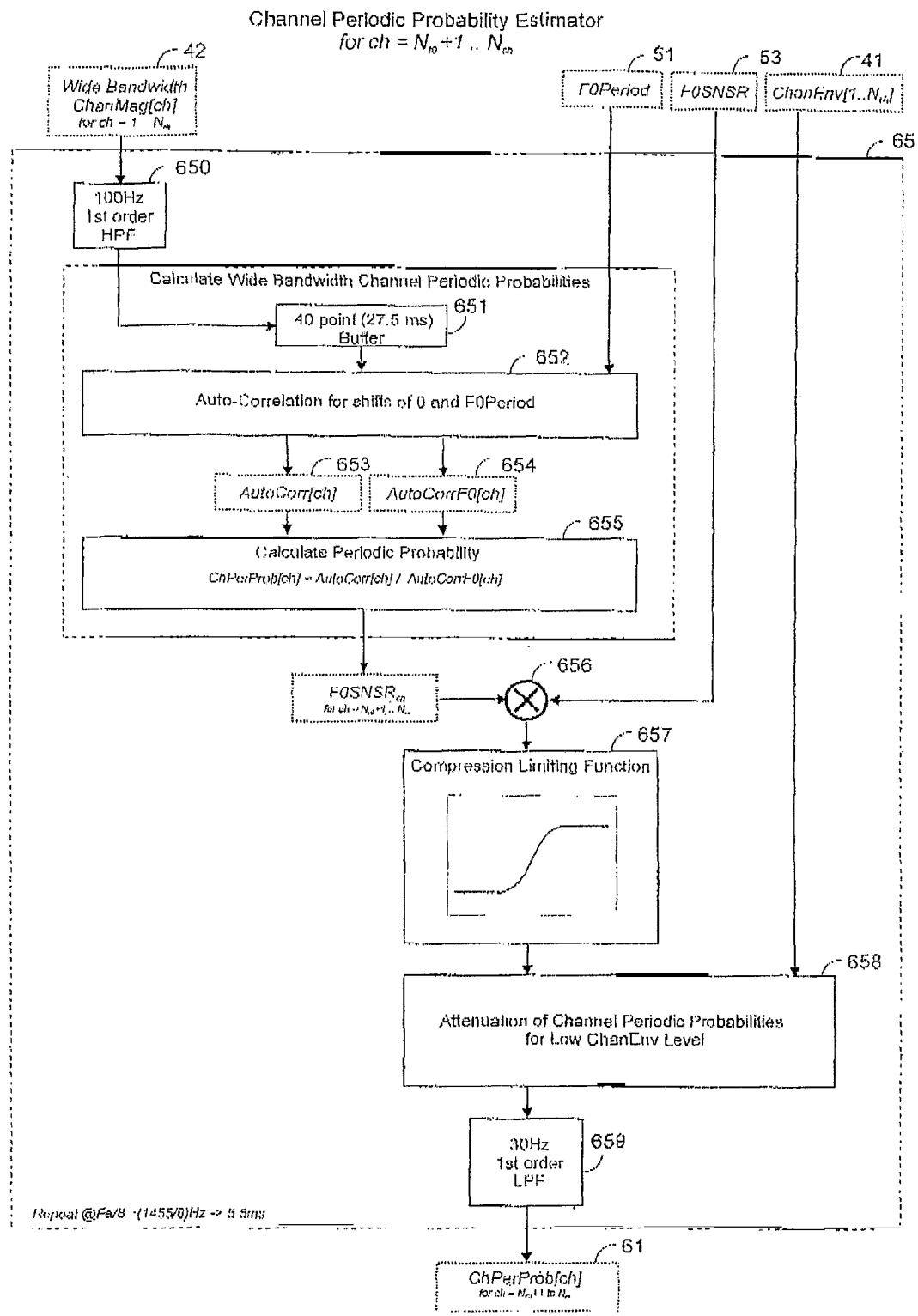
FIG. 11 is a further flow chart showing one embodiment of the process undertaken by the Periodic Probability Estimator of FIG. 8 to estimate the channel periodic probability for each channel that has a centre frequency greater than 2 kHz.

Referring to FIG. 11, for frequency channels above the frequency range analysed by the F0 Estimator (typically >2 kHz), the channel periodic probability is estimated by method 65 of the PPE 6 by determining whether the period of the channel envelope signal is equal to (or close to) the period of the estimated F0 frequency. This is achieved by high-pass filtering in step 650 (using a $1^{st}$ order 100 Hz high-pass filter) the wide-bandwidth channel envelope signal 42 (Wide, bandwidth ChanMag) obtained from the Filterbank 4, and maintaining a history of it in a buffer 651 of approximately 28 ms (40 samples) duration.

For each channel, the most recent 20 samples (~14 ms) of the buffer contents are auto-correlated in step 652 using time shifts of zero and the estimated F0 period 51 obtained from the F0 Estimator 5. The ratio of the F0 period-time shifted auto-con-elation value 654 over the zero-time shifted auto-correlation value 653 is determined in step 655 using the following equation, for n=12 to $N_{ch}$ typically, where HPF is (be high pass filler function and ACF(f, l) is the auto-correlation function of f for a lag l.

$$F0SNSR_{ch}[n] = \frac{ACF(HPF(WideBandWidthChanMag[n]), F0Period)}{ACF(HPF(WideBandWidthChanMag[n]), 0)}$$

For auto-correlation ratios close to 1.0, a high channel power-to-total power ratio is estimated, whereas for values of 0.5 or lower, a low channel power-to-total power is estimated. In step 656, this result is normalised (i.e. multiplied) by the F0SNSR value. In step 657, the result is trans formed using a non-linear compression-limiting (or sigmoid) function, as per the equation referred to above in step 644, where the sigmoid function has an inflection point a=0.35, and a width b=0.5. In step 658, a scaling function is then used to reduce the channel periodic probability value for cases when the slow-varying envelope of the channel signal 41 is low (as per the same procedure described above in step 645). Finally, the channel periodic probability value is low-pass filtered in step 659 using a $1^{st}$ order 30 Hz LPF to derive the channel periodic probability 61 (ChPerProb) for each channel (>2 kHz typically).

As shown in FIG. 2, the PPE 6 provides the Periodic Probability 60 (PerProb) and the Channel Periodic Probability 61 (ChPerProb) to the Channel Modulator 7 to be used to apply F0 modulation to the slow-varying envelope signal of each frequency channel 41 (ChanEnv) and to combine or mix these signals with the non-modulated channel envelope signals.

Figure 12:
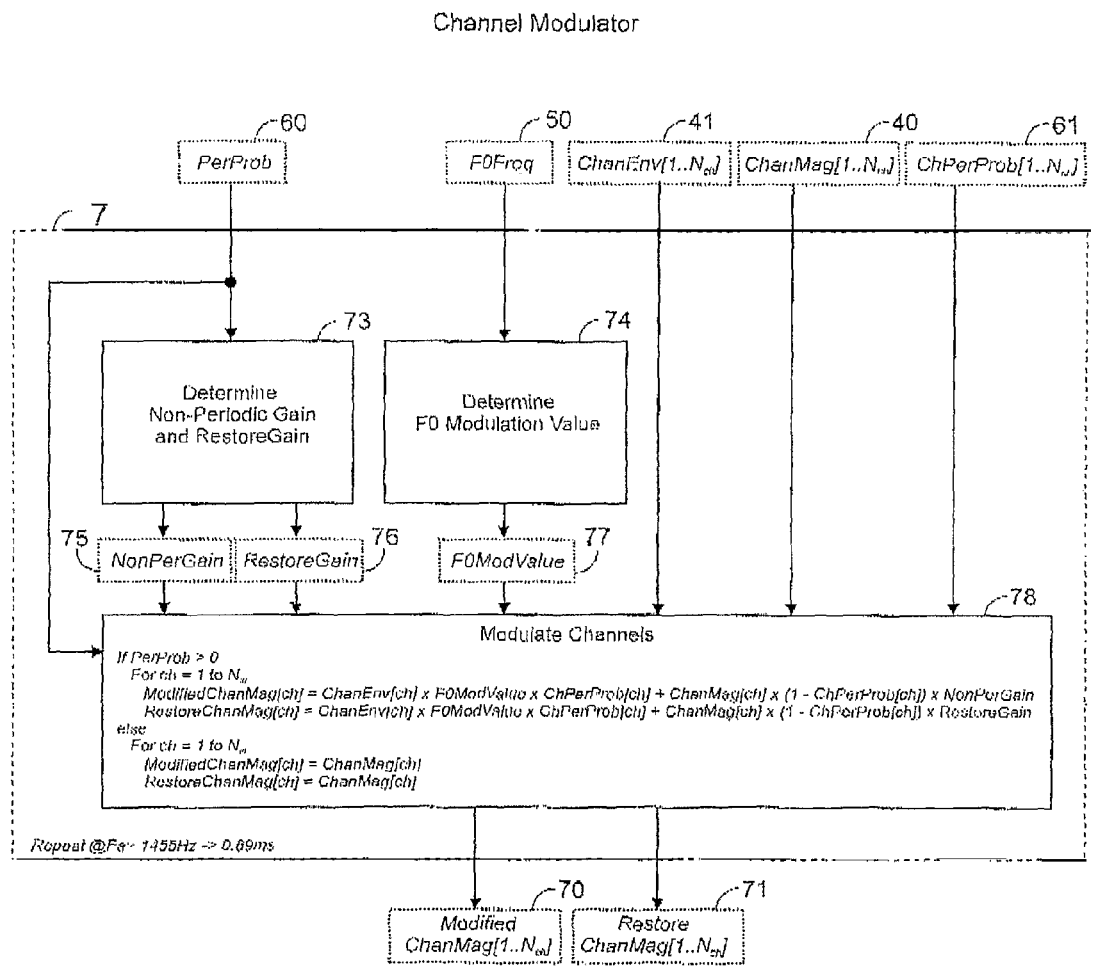
FIG. 12 is a schematic diagram showing one embodiment of the various components of a Channel Modulator in accordance with the system of the present invention.

Referring to FIG. 12, the slow-varying envelope signal (ChanEnv) 41 of each frequency channel is modulated by a modulation function 77 (M) of frequency equal to the estimated F0 frequency 50 and is then mixed with the channel envelope signal 40 (ChanMag) to provide the modified channel envelope signal 70 (Modified ChanMag) 70. The mixing ratio for these two signals is derived from each channels periodic probability 61 (ChPerProb), where a high probability mixes in a high ratio of the F0 modulated-to-non modulated signals and a low probability mixes in a low ratio of these signals. In general, channels that have a high channel periodic probability 61 will receive a modulated-to-non modulated mixing ratio close to 1.0. In contrast, channels that have a low channel periodic probability will receive a modulated-to-lion modulated mixing ratio close to 0. This is achieved in step 78 where the F0 modulation function M is used to modulate the slow varying channel envelope signals 4 (ChanEnv) multiplied by the channel periodic probability 61 (ChPerProb). In this regard, the modulated slow-varying envelope signal in each frequency channel is scaled by the channel periodic probability. The unmodulated channel envelope signals 40 (ChanMag) are scaled by the channel non-periodic probabilities (i.e., 1−ChPerProb) multiplied by the NonPerGain 75 and mixed with the F0 modulated channel signals as per the following equation;

ModifiedChanMag[n]=ChanEnv[n]×ChPerProb[n]×M(F0Freq)+ChanMag[n]×(1−ChPerProb[nJ)×NonPerGain for channels n=1 to $N_{ch}$ The modified channel envelope signals 70 (Modified-ChanMag) are then passed to the maxima, selection stage where processing continues.

In addition, for each frequency channel, the modulated slow-varying envelop signal is mixed with the envelope signal in each frequency channel 40 (ChanMag) sealed by the restoration gain 76 (RestoreGain) multiplied by one minus the channel periodic probability 61. The result is output as the restore channel envelope signal 71 (Restore ChanMag) as per the following equation;

RestoreChanMag[n]=ChanEnv[n]×ChPerProb[n]×M(F0Freq)+ChanMag[n]×(1−ChPerProb[n])×RestoreGain for channels n=1 to $N_{ch}$ The non-periodic gain 75 (NonPerGain) and restore gain 76 (RestoreGain) values are used to control the level of non-periodic components in the modified and restore channel envelope signals, particularly for channels that have low channel periodic probabilities. These values are determined in step 73 using the input signal periodic probability 60 (PerProb). Typically, RestoreGain=0.8 (i.e., −2 dB). For "quiet conditions" NonPerGain=PerProb×0.5+(1−PerProb)×RestoreGain, whereas for "noisy conditions" NonPerGain=PerProb×0.1+(1−PerProb)×RestoreGain. These values range from 0.0 to 1.0 and thus actually attenuate non-periodic components in the modified and restore channel envelope signals particularly when the input signal periodic probability value (PerProb) is high (i.e. periodic).

The F0 Modulation function 77 (M) determined in step 74 employs a low duty cycle so that the coded stimulus envelope approaches that of a non-modulated, F0-rate, pulse-train. This function was chosen because the pitch elicited by electrical pulse trains is governed by a function of the longest first-order intervals between pulses rather than the period of modulation. The modulation function consists of a narrow pulse with an instantaneous attack time and an exponential decay and is stored as a single cycle (period) consisting of 128 samples. Control is provided to adjust the depth of the modulation function and its exponential decay rate. By default, the modulation depth MD (defined as peak/trough stimulation level in clinical current units) is adjusted to 0.5 of a subjects' electrical DR which translates to an acoustic-equivalent depth of 20 dB given a 40 dB DR in each channel. In addition, the exponential decay function falls to 10% of its' peak value within the first quarter of the modulation period. The modulation fund ion is sampled at an interval of F0×128 samples divided by the stimulation rate of the system (1455 Hz). However, because the stimulation rate can be a non-integer multiple of F0, amplitude beating in the sampled output can arise. To avoid this, at the beginning of every F0 cycle, sampling of the modulation function is reset so that the first sample of the cycle always aligns with the first sample (i.e., peak pulse level) of the modulation function. The start of each F0 cycle is determined by maintaining an accurate ongoing record of the desired. F0 modulation phase.

Referring again to FIG. 2, the modified channel envelope signal 70 (Modified ChanMag) and the restore channel envelope signal 71 (Restore ChanMag) generated by the channel modulator are sent to the Maxima selector 8. The Maxima selector 8 incorporates optional processing to improve selection of channels containing harmonics of F0, particularly in noise conditions, so that differences in the channels selected for stimulation between the present invention and a typical. CT system can be minimised. Maxima (i.e. the channels with the largest spectral magnitude) are selected from the modified channel magnitude values 70 (Modified ChanMag) which are derived from modulation of the slow-varying channel envelope signals 41 (ChanEnv) as described above. This contrasts from conventional CI systems, where the maxima are selected directly from the channel envelope signals 40 (ChanMag) which carry greater temporal variation (i.e. higher envelope frequencies) than the slow-varying channel envelope signals. The lower temporal variation in the slow-varying envelope signals processed by the Maxima selector 8 of the present invention means there will be less variation in the spectral magnitude overtime and thus lower variation in the channels selected as maxima can result. To compensate for this, the present invention incorporates an optional scheme in which selection of maxima is partially multiplexed across frames so as to increase the spectral range of maxima selected and thereby introduce a greater spread in the selected maxima channels.

In addition, because the Maxima selector 8 selects maxima from the modified channel magnitude values 70 (Modified ChanMag) in which channel signals that are "non-periodic" are attenuated (e.g., using the NonPerGain parameter), processing is provided so that the magnitude of attenuated non-periodic channel signals can be restored after the maxima selection process by using the restore channel magnitude values 71 (Restore ChanMag).

Figure 13:
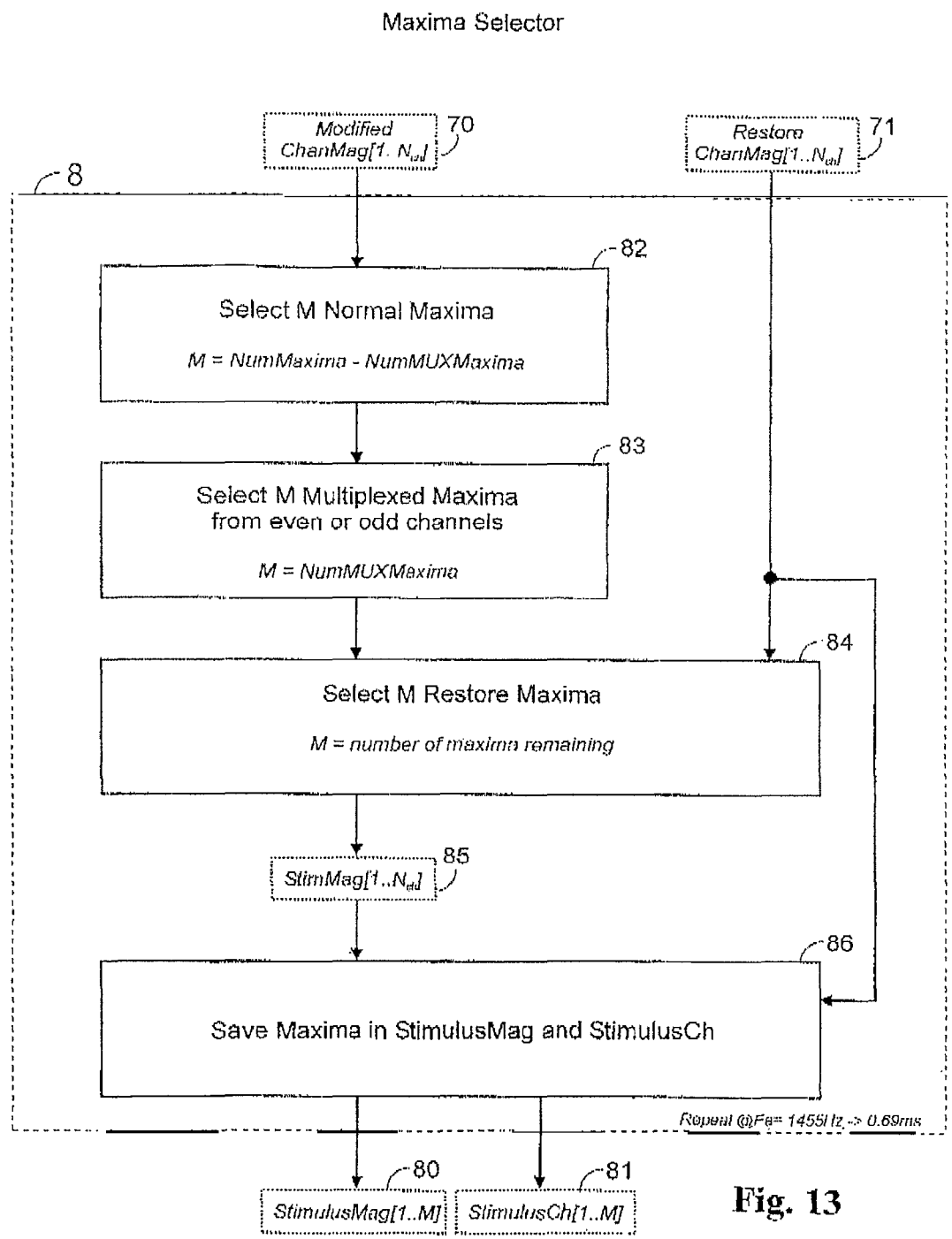
FIG. 13 is a flow chart showing one embodiment of the process undertaken by the maxima selector to determine stimulus channels and stimulus magnitudes for the stimulator.

Referring to FIG. 13, the Maxima selector 8 incorporates three-passes of maxima selection (i.e. selection of the frequency channels that have the highest envelope values in any one time frame). The first pass, shown at step 82, selects maxima from the modified channel envelope signals 70 (Modified ChanMag) in the same way as is normally done in existing CI systems. However, rather than selecting up to NumMaxima (typically 10 for a rate of 1455 Hz) maxima, the number of maxima selected is reduced by NumMUXMaxima (typically 2) so that selection of maxima can be multiplexing across frames and thereby increase the spectral range of maxima selected. For instance, if NumMuxima=10 and NumMUXMaxima=2, then up to 8 maxima are selected in the first pass, allowing for selection of 2 more maxima in the second pass.

In the second pass, shown at step 83, NumMUXMaxima are selected but only from either the even or odd numbered frequency channels in any one pass. Selection from even or odd channel numbers is alternated between frames. This process increases the range of channels that can be selected as maxima over two consecutive frames by NumMUXMaxima (e.g., from 10 to 12).

In the third and final pass, shown at step 84, if less than NumMaxima maxima have actually been selected (note, this arise if many channel envelope signals are below the threshold level of stimulation because these channels are typically precluded from being selected as maxima), the remaining maxima are selected from the restore channel envelope signals 71 (Restore ChanMag).

Finally, at step 86, the selected maxima channel numbers are used to define the channel numbers for subsequent stimulation of electrodes 81 (StimulusCh). The stimulation magnitude 80 (StimulusMag) is derived optionally from either the selected channel magnitude values 85 or from the restore channel envelope signals 71 (Restore ChanMag) that correspond to each selected maxima channel. Deriving the stimulation magnitudes from the restore channel envelope signals allows the magnitude of non-periodic components in channel signals with low periodic probabilities to be restored to their normal level (or typically to −2 dB of their level for Restore-Gain=0.8) after they have been selected as maxima. The purpose of attenuating them before maxima selection (i.e., in step 78) is to reduce the probability of them being selected as maxima in preference to channels that contain periodic component's.

Referring again to FIG. 2, the Mapping-Encoder 9 receives the acoustic stimulus levels 80 (StimulusMag) for each selected stimulus channel 81 (StimulusCh) and converts this information into electrical current level values for each selected electrode respectively based on the individual CI recipients electrical threshold and comfortable levels of stimulation in accordance with conventional methods. The stimulus data is then encoded into radio-frequency (RF) packets to be sent by the RF transmitter 10 to the implanted cochlear stimulator 11 which activates (stimulates) the cochlea electrodes based on the decoded stimulus data stream.

It will be appreciated that the system of the present invention is directed towards providing a complete system that codes voice and/or musical pitch information in a cochlear implant system in an effective manner, and which is robust to the effects of competing noise and/or interfering signals. This is achieved by applying different processes to different listening situations, ranging from listing situations comprising complex harmonic input signals, non-harmonic input signals, and varying combinations of both non-harmonic and harmonic input signals.

In this regard, the system of the present invention caters for situations comprising complex-harmonic input signals (i.e., signals that comprise two or more harmonics (or partials) of a fundamental frequency, e.g., a voiced vowel in speech or a musical sound played by a tonal instrument), by modulating the low-frequency (or slow-varying) envelope of the electrical stimulus signal in each frequency channel by a periodic function of frequency equal to the most dominant, fundamental frequency (F0) present in the input sound.

The system of the present invention caters for situations comprising non-harmonic input signals (e.g., an unvoiced consonant in speech or a sound played by a percussive instrument) by identifying such a situation and deriving the electrical stimulus signal in each channel in a manner consistent with conventional CI sound processing strategies (i.e. from the non-modulated envelope signals in each frequency channel).

The system of the present invention is specifically adept at catering for many real world listening situations, namely where the input sound contains a time varying combination of harmonic and non-harmonic signals distributed across the frequency spectrum. Upon detection of such situations by the present invention, the system dynamically combines (mixes) the F0-modulated signal and non-modulated signal in each frequency channel together based oil the degree to which the channel signal is related to most dominant F0 (i.e., contains a frequency component equal to an integer multiple of F0) in the input sound. A harmonic (or periodic) probability is determined for each frequency channel which is used to control the ratio of F0 modulated-to-non modulated gain for generation of each channel signal.

Figure 14A:
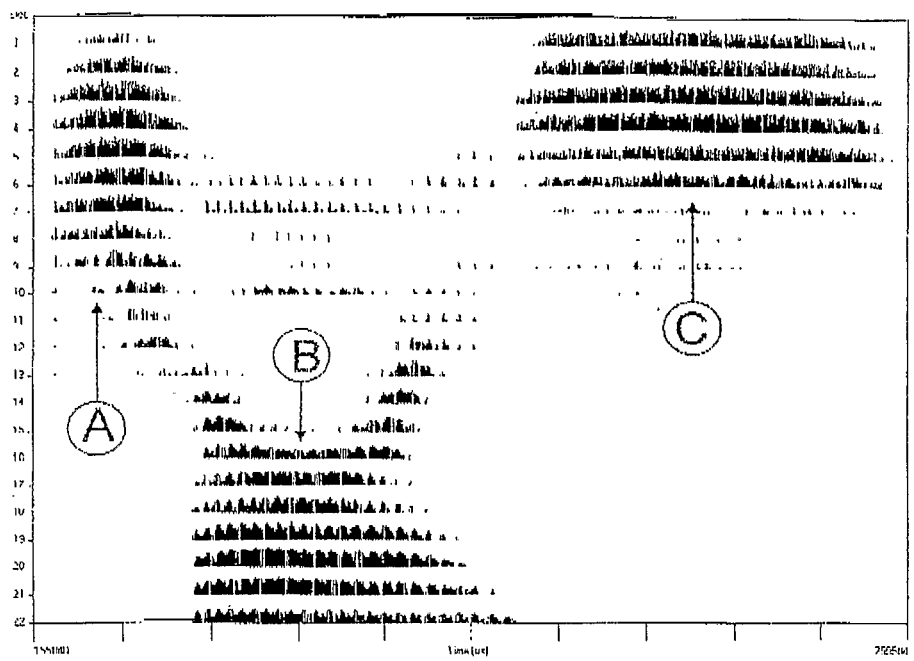
FIG. 14a and 14b show electrodograms for a standard CI processing strategy and the processing strategy of the present invention respectively.
Figure 14B:
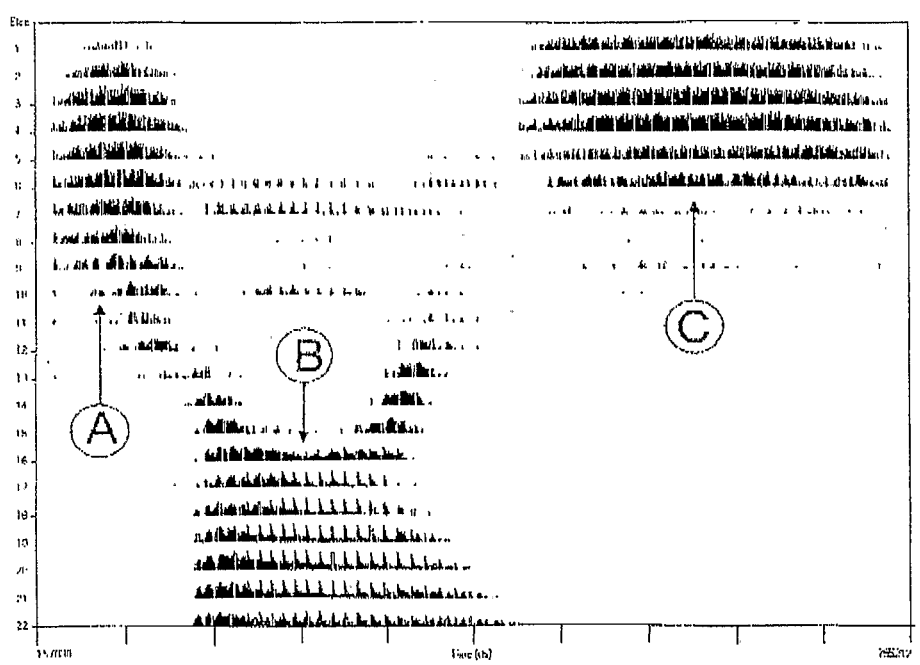

Referring to FIGS. 14a and 14b, electrical stimulus output patterns, known as electrodograms, which are similar to spectrograms for acoustic signals, but plot stimulus intensity (as log current level), for each, electrode (channel) as a function of time, are provided to demonstrate the functionality of the present invention.

FIG. 14a represents an electrodogram for an existing CI sound processing strategy, known as the Advanced Combinational Encoder (ACE) strategy, whilst FIG. 14b represents an electrodogram for the sound processing strategy of the present invention. The speech token processed by each strategy in these electrodogram recordings was the word "choice" spoken by a male speaker having an F0 frequency of approximately 118 Hz.

It can be seen that for the voiced vowel, identified as B and representative of a complex-harmonic input signal, the stimulus envelope in FIG. 14b has been modulated by a periodic function of frequency equal to the F0 of the speaker. As such, it differs considerably from the stimulus envelope in FIG. 14a, where no, or very little, modulation has occurred.

This contrasts from the unvoiced consonants, identified as A and C and representative of non-harmonic input signals, whereby the stimulus signals in FIGS. 14a and 14b are substantially identical.

It will be appreciated that the process and system of the present invention is able to more effectively process sound in real situations, namely those that can simultaneously comprise both harmonic and non-harmonic components. For harmonic sound signals, such as purely complex-harmonic signals such as signals that contain two or more harmonics of F0 as is the case with a voiced vowel or a musical sound played by a tonal instrument, the slow-varying envelope of the stimulus signal in each channel is modulated by a periodic function of frequency equal to F0. For non-harmonic signals such as an unvoiced consonant or a percussive sound, the electrical stimulus signal in each channel is essentially derived using traditional methods and thus consists of a narrow-band/noise envelope signal. Thus, in listening situations comprising both harmonic and non-harmonic components of the sound, signal, for each channel signal a mixture of the F0 modulated and non-modulated envelope signal is coded. The mixing ratio of these signals is determined by the degree to which the channel signal is related to the most dominant F0 in the sound, whereby a strong relationship results in a high mixing ration of the F0-modulated-to-non modulated signal and wherein a weak relationship results in a low ratio.

It will thus be appreciated that the sound processing system of the present invention is able to detect and process sound signals to take into consideration different listening situations encountered in everyday situations to provide users of the system with improved perception of voice pitch and musical tone, whilst dealing with the effects of competing noise and/or interfering signals in an effective manner.

Throughout the specification and claims the word "comprise" and its derivatives are intended to have an inclusive rather than exclusive meaning unless the contrary is expressly stated or the context requires otherwise. That is, the word "comprise" and its derivatives will be taken to indicate the inclusion of not only the listed components, steps or features that it directly references, but also other components, steps or features not specifically listed, unless the contrary is expressly stated or the context requires otherwise.

If will be appreciated by those skilled in the art that many modifications and variations may be made to the methods of the invention described herein without departing from the spirit and scope of the invention.

The claims defining the invention are as follows:

1. A method for processing sound signals for use in a hearing prosthesis, comprising:
    converting said sound signal into an electrical signal;
    processing said electrical signal into a plurality of frequency channel signals, each frequency channel signal having an amplitude envelope to define at least one set of channel outputs, wherein processing the electrical signal into a plurality of frequency channel signals includes:
        passing the electrical signal through a first bank of band pass filters; and
        passing the electrical signal through an envelope detector to produce a set of corresponding channel envelope signals as a set of first channel outputs, wherein each channel envelope signal of the set of first channel outputs is smoothed in time by a channel envelope tracker to derive slow moving channel envelope signals as a set of second channel outputs;
    obtaining information relating to a fundamental frequency of the electrical signal;
    obtaining information relating to a harmonic nature of the electrical signal;
    modulating the at least one set of channel outputs in accordance with the information relating to the fundamental frequency and the harmonic nature of the electrical signal so as to generate at least one modified set of channel outputs; and
    selecting one or more channels from the at least one modified set of channel outputs to define at least one or more channels for electrical stimulation by a corresponding electrode of the hearing prosthesis, as well as the magnitude of said electrical stimulation.

2. A method according to claim 1, wherein the step of converting said sound signal into an electrical signal includes employing a microphone to detect and convert the sound signal into an electrical signal wherein the electrical signal is amplified and sampled by passing the electrical signal through an analog-to digital converter to generate a sampled signal.

3. A method according to claim 1, further comprising passing the electrical signal through a second bank of band pass filters, wherein the second bank of band pass filters have substantially the same centre frequencies as the first bank of band pass fillers and are sufficiently wide so as to pass at least two fundamental frequency harmonics of the highest fundamental frequency determined in relation to the electrical frequency to produce a plurality of wide-bandwidth channel signals as a third set of channel outputs.

4. A method according to claim 3, wherein the step of obtaining information relating to the fundamental frequency of the electrical signal comprises passing the electrical signal through a Fundamental Frequency Estimator.

5. A method according to claim 4, wherein the Fundamental Frequency Estimator is a phase-vocoder FFT filter bank that processes the electrical signal to provide an estimate of the frequency and power of any sinusoidal frequency components present in the electrical signal up to a frequency of around 2 kHz.

6. A method according to claim 5 wherein the Fundamental Frequency Estimator determines the fundamental frequency of the most dominant harmonic signal detected in the electrical signal up to a frequency of around 2 kHz and generates a signal representative of the estimation of the most dominant fundamental frequency.

7. A method according to claim 5 wherein the step of obtaining information relating to the harmonic nature of the electrical signal comprises passing at least the signal representative of the ratio of the power related to the most dominant fundamental frequency to the total signal power present in the electrical signal to a Periodic Probability Estimator.

8. A method according to claim 7, wherein the harmonic nature of the electrical signal is determined by the Periodic Probability Estimator which estimates the probability that the signal in any frequency channel is related to the estimated most dominant fundamental frequency of the electrical signal and generates a channel periodic probability signal for each channel using the frequency and power of any sinusoidal frequency components present in the electrical signal determined from the Fundamental frequency Estimator, and the set of third channel outputs determined by the second bank of band pass filters.

9. A method according to claim 1, wherein the step of modulating the at least one set of channel outputs in accordance with the information relating to the fundamental frequency and the harmonic nature of the electrical signal so as to generate at least one modified set of channel outputs is performed by a channel modulator.

10. A method of processing sound signals for use in a hearing prosthesis, comprising:
converting said sound signal into an electrical signal;
processing said electrical signal into a plurality of frequency channel signals, each frequency channel signal having an amplitude envelope to define at least one set of channel outputs;
determining whether the electrical signal comprises harmonic and/or non-harmonic signals;
for portions of the electrical signal comprising harmonic signals, modulating a slow varying envelope of the channel outputs by a periodic function of frequency equal to the fundamental frequency of the harmonic signal to produce one or more modulated channel envelope signals;
for portions of the electrical signal comprising non-harmonic signals, producing one or more non-modulated channel envelope signals;
for each channel, mixing the modulated channel envelope signal and the non-modulated channel envelope signal in accordance with a predetermined mixing ratio to produce a mixed channel stimulation signal for each channel; and
selecting one or more channels to define at least one or more channels for electrical stimulation and applying stimulation to a corresponding electrode of the hearing prosthesis, in accordance with the mixed channel stimulation signal.

11. A method according to claim 10, wherein the predetermined mixing ratio is derived from a degree to which the frequency channel signal is related to the most dominant fundamental frequency in the electrical signal.

12. A system for processing sound signals for use in a hearing prosthesis, the system comprising:
a transducer for converting a sound signal into an electrical signal;
a first processor for processing said electrical signal into a plurality of frequency channel signals, each channel signal having an amplitude envelope to define at least one set of channel outputs, wherein the first processor comprises:
a first bank of band pass filters to process the electrical signal into a plurality of frequency channel signals;
an envelope detector such that each channel signal is further passed through the envelope detector to produce a set of corresponding channel envelope signals as a set of first channel outputs; and
a channel envelope tracker connected to receive each channel envelope signal of the set of first channel outputs to derive slow moving channel envelope signals as a set of second channel outputs;
a second processor for obtaining information relating to a fundamental frequency of the electrical signal;
a third processor for obtaining information relating to the harmonic nature of the electrical signal;
a modulator for modulating the at least one set of channel outputs received from the first processor in accordance with the information relating to the fundamental frequency and the harmonic nature of the electrical signal so as to generate at least one modified set of channel outputs;
a selector for selecting one or more channels from the at least one modified set of channel outputs so as to define at least one or more channels for electrical stimulation together with the magnitude of said electrical stimulation and generating a stimulation signal in accordance therewith; and
a transmitter for transmitting said stimulation signal for application by said hearing prosthesis.

13. A system according to claim 12, wherein the transducer comprises a microphone configured to detect and convert the sound signal into an electrical signal.

14. A system according to claim 12, further comprising a second bank of band pass filters, wherein the second bank of band pass filters have substantially the same centre frequencies as the first bank of band pass filters and are sufficiently wide so as to pass at least two fundamental frequency harmonics of the highest fundamental frequency determined in relation to the electrical frequency to produce a plurality of wide-band width channel signals.

15. A system according to claim 14, wherein the second processor comprises a Fundamental Frequency Estimator.

16. A system according to claim 15, wherein the Fundamental Frequency Estimator is a phase-vocoder FFT filter bank that processes the electrical signal to provide an estimate of the frequency and power of any sinusoidal frequency components present in the electrical signal up to a frequency of around 2 kHz.

17. A system according to claim 16, wherein the Periodic Probability Estimator is operable by the third processor and further estimates the probability that the signal in any frequency channel is related to the estimated most dominant fundamental frequency of the electrical signal and generates a channel periodic probability signal for each channel using the frequency and power of any sinusoidal frequency components present in the electrical signal determined from the Fundamental frequency Estimator and the set of third channel outputs determined by the second bank of band pass filters.

18. A system according to claim 12, wherein the modulator is a channel modulator that receives the set of second channel outputs and modulates said set of second channel outputs by a periodic modulation function substantially equal to the estimated most dominant fundamental frequency of the electrical signal as provided by the Fundamental Frequency Estimator.

19. A system according to claim 18, wherein the modulated set of second channel outputs are scaled by the channel periodic probability signals determined by the Periodic Probability Estimator for each channel to produce a scaled and modulated set of second channel outputs.

20. A system according to claim 12, wherein the selector is a maxima selector that selects, one or more channels from the at least one modified set of channel outputs based upon the outputs having a largest spectral magnitude.

21. A system according to claim 12, wherein the transmitter comprises an encoder that encodes the stimulation signal for transmission to an implanted stimulator.

* * * * *